United States Patent
Hageman et al.

(10) Patent No.: US 7,344,846 B2
(45) Date of Patent: Mar. 18, 2008

(54) DIAGNOSTICS AND THERAPEUTICS FOR MACULAR DEGENERATION-RELATED DISORDERS

(75) Inventors: Gregory S. Hageman, Coralville, IA (US); Robert F. Mullins, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/205,370

(22) Filed: Aug. 16, 2005

(65) Prior Publication Data
US 2005/0287601 A1 Dec. 29, 2005

Related U.S. Application Data

(63) Continuation of application No. 10/084,639, filed on Feb. 25, 2002, now Pat. No. 7,011,952, which is a continuation-in-part of application No. 09/845,745, filed on Apr. 30, 2001, now abandoned, which is a continuation-in-part of application No. 09/510,230, filed on Feb. 22, 2000, now abandoned.

(60) Provisional application No. 60/200,698, filed on Apr. 29, 2000.

(51) Int. Cl.
G01N 33/564 (2006.01)
(52) U.S. Cl. .................... 435/7.21; 435/7.4; 435/7.93; 435/7.95; 436/506; 436/507
(58) Field of Classification Search ............... 435/7.21, 435/7.4, 7.93, 7.95; 436/506, 507
See application file for complete search history.

(56) References Cited

U.S. PATENT DOCUMENTS

| | | | |
|---|---|---|---|
| 3,654,090 A * | 4/1972 | Schuurs et al. ............ | 435/7.93 |
| 5,405,749 A * | 4/1995 | Polans et al. ............. | 435/7.23 |
| 5,472,939 A | 12/1995 | Fearon et al. | |
| 5,681,571 A | 10/1997 | Holmgren et al. | |
| 5,686,598 A | 11/1997 | North et al. | |
| 5,705,380 A | 1/1998 | North et al. | |
| 5,773,573 A | 6/1998 | Holms | |
| 5,843,449 A | 12/1998 | Boots et al. | |
| 5,951,984 A | 9/1999 | Kaneko et al. | |
| 6,087,120 A | 7/2000 | Van Oeveren et al. | |
| 6,103,235 A | 8/2000 | Neville et al. | |
| 6,153,203 A | 11/2000 | Holmgren et al. | |
| 7,011,952 B2 * | 3/2006 | Hageman et al. ......... | 435/7.21 |
| 2002/0015957 A1 | 2/2002 | Hageman et al. | |
| 2002/0102581 A1 | 8/2002 | Hageman et al. | |
| 2003/0207309 A1 | 11/2003 | Hageman et al. | |

FOREIGN PATENT DOCUMENTS

| WO | WO 90/15152 A1 | 12/1990 |
|---|---|---|
| WO | WO 95/17673 A1 * | 6/1995 |
| WO | WO 97/38004 A1 | 10/1997 |
| WO | WO 00/52479 A2 | 9/2000 |

OTHER PUBLICATIONS

Chen, H. et al. "An immunologic study of age-related macular degeneration" Yan Ke Xue Bao, Sep. 1993, pp. 113-120, vol. 9, No. 3.*
Gurne, D. et al; "Antiretinal Antibodies in Serum of Patients with Age-related Macular Degeneration", Opthalmology; May 1991; pp. 602-607, vol. 98, No. 5.*
Penfold, P. et al; "Autoantibodies to retinal astrocytes associated with age-related macular degeneration", Graefe's Archive for Clinical and Experimental Ophthalmology, 1990, pp. 270-274, vol. 228.*
Access. No. 87011665 MEDLINE, Doc. No. PubMed ID: 2428981, "An enzyme immunoassay for auto-antibodies to keratin in normal human serum and in pleural fluids from patients with various malignant or non-malignant lung diseases", Lambre et al, Journal of clinical & laboratory immunology, (1986) vol. 20, No. 4, pp. 171-176.*
Abraha, A. and Luzio, J.; "Inhibition of the formation of the complement membrane-attack complex by a monoclonal antibody to the complement component C8α Subunit", Biochem J, 1989, pp. 933-936; 264, Great Britain.
Akiyama, H. et al; "Inflammation and Alzheimer's disease"; Neurobioy of Aging 21; May-Jun. 2000; pp. 383-421; vol. 21, No. 3.
Allikmets, R. et al; "Mutation of the Stargardt Disease Gene (ABCR) in Age-Related Macular Degeneration", Science, Sep. 19, 1997; pp. 1805-1807, vol. 277.
Auda, G. et al; "Measurement of complement activation products in patients with chronic rheumatic diseases", Rheumatology International; 1990, 10(5):pp. 185-189, Springer-Verlag.
Baatrup, G. et al; "Effects of coagulation temperature on measurements of complement function in serum samples from patients with systemic lupus erythematosus", Annuals of Rheumatic Disease, 1992, 51(7):892-897.
Bachinsky, D. et al; "Detection of Two Forms of GP330", American Journal of Pathology.; Aug. 1993, pp. 598-611, vol. 143, No. 2.
Bhakdi, S. & Tranum-Jensen, J.; "Membrane Damage by Complement", Biochimica et Biophysica Acta; 1983, pp. 343-372; 737, Elsevier Science Publishers B.V.
Bora, N.S. et al.; "Differential expression of the complement regulatory proteins in the human eye", Investigative Ophthalmology & Visual Science; Dec. 1993, pp. 3579-3584, vol. 34, No. 13.
Braley-Mullen; "Activation of Distinct Subsets of T Suppressors Cells with Type III Pheumococcal Polysaccharide Coupled to Syngeneic Spleen Cells", Immunological Tolerance To Self and Non-Self, Annals of New York Academy of Science, 1982, pp. 156-166, vol. 392.
Burger, R. et al; "The C Terminus of the Anaphylatoxin C3a Generated Upon Complement Activation Represents a Neoantigenic Determinant with Diagnostic Potential", Journal of Immunology, Jul. 15, 1988; pp. 553-558, vol. 141 No. 2, Printed in the U.S.A.

(Continued)

*Primary Examiner*—David A. Saunders
(74) *Attorney, Agent, or Firm*—Townsend and Townsend and Crew LLP

(57) ABSTRACT

The invention relates to methods for diagnosing and treating macular degeneration-related disorders. The invention also related to methods for identifying genes that cause macular degeneration-related disorders.

18 Claims, No Drawings

OTHER PUBLICATIONS

Buyon, J. et al.; "Assessment of Disease Activity and Impending Flare in Patients with Systemic Lupus Erythematosus", *Arthritis and Rheumatism*; Sep. 1992, pp. 1028-1037, vol. 35, No. 9.

Campbell, R. et al; "An Anion Binding Study of Vanadyl(IV) Human Serotransferrin", *Journal of Biological Chemistry*, 1977, pp. 5996-6001, vol. 252, No. 17, Printed in the U.S.A.

Caraher, E.M. et al; "Evidence for enhanced rates of complement activation in serum from patients with newly diagnosed insulin-dependent diabetes mellittus exposed to rat islet cells and complement-dependent induction of islet cell apoptosis.", *Journal of Endocrinology*; 1999, pp. 143-153, vol. 162, No. 1, Printed in Great Britain.

Chenoweth, D. et al; "Complement Activation During Cardiopulmonary Bypass", *New England Journal of Medicine*; Feb. 26, 1981; pp. 497-502, vol. 304, No. 9, Printed in the U.S.A.

Chain, B. et al; "Improvement of the vitro T cell proliferation assay by a modified method that separates the antigen recognition and IL-2-dependent steps.", *Journal of Immunological Methods*; 1987, pp. 221-228, vol. 99.

Debrock, S. and Declerck, P.; "Characterization of common neoantigenic epitopes generated in plasminogen activator inhibitor-1 after cleavage of the reactive center loop or after complex formation with various serin proteinases.", *FEBS Letters*; 1995, pp. 243-246, vol. 376.

Delori, F. and Ben-Sira, I.; "Excitation and emission spectra of fluorescein dye in the human ocular fundus.", *Investigative Ophthalmology*; Jun. 1975, pp. 487-492, vol. 14, No. 6.

Delori, F. et al; "In Vivo Fluorescence of the Ocular Fundus Exhibits Retinal Pigment Epithelium Lipofuscin Characteristics", *Investigative Ophthalmology & Visual Science*; Mar. 1995, pp. 718-729, vol. 36, No. 3.

Detrick, B. et al.; "Class II Antigen Expression and Gamma Interferon Modulation of Monocytes and Retinal Pigment Epithelial Cells from Patients with Retinitis Pigmentosa", *Clinical Immunology and Immunopathology*, Aug. 1985, pp. 201-211, vol. 36, No. 2, San Diego, CA, U.S.A.

Edwards, A. et al; "Malattia Leventinese: Refinement of the Genetic Locus and Phenotyic Variability in Autosomal Dominant Macular Drusen", *American Journal of Ophthalmology*; Sep. 1998, pp. 417-424, vol. 126, Elsevier Science Inc.

Egerton, M. et al; "Identification of Ezin as an 81-kDa Tyrosin-Phosphorylated Protein in T Cells", *The Journal of Immunology*, Sep. 15, 1992; pp. 1847-1852, vol. 149, No. 6, Printed in the U.S.A.

Enk, C. et al; "A Standardized Human T-lymphocyte Proliferation Assay for Detecting Soluble Accessory Factors From Monocytes", *Acta Pathol Microbiol Immunol Scand [C]*, 1984, pp. 93-100, vol. 92, No. 2.

Epstein, G.A. and Rabb, M.F.; "Adult vitelliform macular degeneration: diagnosis and natural history"; *British Journal of Ophthalmology*; 1980, pp. 733-740, vol. 64.

Felbor, U. et al; "Adult vitelliform Macular Dystrophy is Frequently Associated With Mutations in the Peripherin/RDS Gene", *Human Mutation*; 1997, pp. 301-309, vol. 10.

Felbor, U. et al; "Autosomal Recessive Sorsby Fundus Dystrophy Revisited: Molecular Evidence for Dominant Inheritance", *American Journal of Human Genetics*; 1997, pp. 57-62, vol. 60.

Fitzgibbon, J. et al; "Localisation of the human blue cone pigment gene to chromosome band 7q31.3-32", *Human Genetics*; 1994, pp. 79-80, vol. 93.

Forstrom, J.W. et al; Immunization to a syngeneic sarcoma by a monoclonal auto-anti-idiotypic antibody, *Nature*; Jun. 16, 1983; pp. 627-629, vol. 303.

Giltay, R. et al; "Sequence, Recombinant Expression and Tissue Localization of Two Novel Extracellular Matrix Proteins, *fibulin-3* and *fibulin-4*", Matrix Biol, Oct. 1999, pp. 469-480, vol. 18, No. 5.

Gorski, J; "Quantitation of Human Complement Fragment C4ai in Physiological Fluids by Competitive Inhibition Radioimmune Assay", *Journal of Immunological Methods*; 1981, pp. 61-73, vol. 47, Elsevier/North-Holland Biomedical Press.

Goslings W., et al.; "Membrane-Bound Regulators of Complement Activation in Uveal Melanomas. CD46, CD55, and CD59 in Uveal Melanormas"; *Investigative Ophthalmology & Visual Science*, Aug. 1996, pp. 1884-1891, vol. 37, No. 9.

Green, W.R.; "Histopathology of age-related macular degeneration", *Molecular Vision*, Nov. 1999, vol. 5, No. 27.

Griesinger, I.B. et al; Macular Degeneration with Highly Variable Phenotype Localized to Chromosome 6q. *American Journal of Human Genetics*; 63:A30; 1998.

Halliday, W.J. and Maluish, A.E.; Chapter 1: "Hemocytometer LAI: Immunological Basis and Applications", *Assessment of Immune Status by the Leukocyte Adherence Inhibition Test*; 1982; pp. 1-26, Academic Press, Inc; New York.

Hayamizu et al; "Monocyte-derived dendritic cell precursors facilitate tolerance to heart allografts after total lymphoid irradiation", *Transplantation*, 1998, pp. 1285-1291, vol. 66, No. 10.

Hintner, H. et al; "Vitronectin Shows Complement-Independent Binding to Isolated Keratin Filament Aggregates", *Journal of Investigative Dermatology*; Nov. 1989, pp. 656-661, vol. 93, No. 5.

Holz, F. et al.; "Patterns of increased in vivo fundus autofluorescence in the juctional zone of geographic atrophy of the retinal pigment epithelium associated with age-related macular degeneration.", *Graefes Arch Clin Exp Ophthalmol*; 1999, pp. 145-152, vol. 237.

Hugli, T.E. and Chenoweth, D.E.; "Biologically Active Peptides of Complement: Techniques and Significance of C3a and C5a Measurements", *Immunoassays: Clinical Laboratory Techniques for the 1980s*; 1980, pp. 443-460.

Inglehearn, et al; Letter to the Editor entitled, "Loci for Autosomal Dominant Retinitis Pigmentosa and Dominant Cystoid Macular Dystrophy on Chromosome 7p Are Not Allelic", *American Journal of Human Genetics*; 1994, pp. 581-582, vol. 55.

Johnson, L.V. et al.; "A Potential Role for Immune Complex Pathogenesis in Drusen Formation"; *Exp Eye Res*, 2000; pp. 441-449, vol. 70.

Kakehashi, et al; "Differential Diagnosis of Macular Breaks By Microperimetry Using the Scanning Laser Ophthalmoscope", *Jpn J Ophthalmol*; 1996, pp. 116-122; vol. 40, No. 1.

Kaluzny; et al; "The use of indocyanine green angiography in diagnosis of occult choroidal neovascularization in age-related macular degeneration" (title translated), *Klinika Oczna*; 1999, pp. 355-359, vol. 101, No. 5, with abstract.

Kazeem, A.A. et al. et al. "Assay of Circulating Immune Complexes by Immunonephelometry Markers of Immunonephropathy Among Young Nigerians", *East African Medical Journal*, Jun. 1990, pp. 396-403, vol. 67, No. 6.

Kelsell, R. et al; Letter to the Editor entitled, "Localization of a Gene (CORD7) for a Dominant Cone-Rod Dystrophy to Chromosome 6q", *American Journal of Human Genetics*, 1998, pp. 274-279, vol. 63.

Kiang, J. et al, "17 β-Estradiol-induced Increases in Glucose-regulated Protein 78kD and 94kD Protect Human Breast Cancer T47-D Cells from Thermal Injury", *Chinese Journal of Physiology*; 1997, pp. 213-219, vol. 40, No. 4.

Kilpatrick, J. and Volanakis, J.; "Opsonic Properties of C-Reactive Protein. Stimulation by Phorbolmyristate Acetate Enables Human Neutrophils to Phagocytize C-Reactive Protein-Coated Cells", *The Journal of Immunology*, May 1985, pp. 3364-3370, vol. 134, No. 5.

Kita, T. et al; "Atroscierosis V: The Fifth Saratoga International Conference. Oxidized-LDL and Atherosclerosis Role of LOX-1", *Annals of the New York Academy of Sciences*; 2000, pp. 95-100, vol. 902.

Klein, M. et al; "Age-Related Macular Degeneration. Clinical Features in a Large Family and Linkage to Chromosome 1q.", *Arch. Ophthalmol*; Aug. 1998, pp. 1082-1088, vol. 116.

Kohno, T. et al.; "Detection of Choroidal Neovascularization in Age-related Macular Degeneration Using Subtraction Methods in Indocyanine Green Angiography", *Bull Soc Belge Ophtalmol*; 1995, pp. 81-88, vol. 259.

Koppi, T. and Halliday, W.J.; "Further Characterization of the Cells Involved in Leukocyte Adherence Inhibition with Murine Tumor Extracts", *Cellular Immunology*; 1982; pp. 394-406, vol. 66.

Kovacs, H. et al; "Evidence That C1q Binds Specifically to $C_h2$-like Immuinoglobulin γ Motifs Present in the Autoantigen Calreticulin and Interferes with Complement Activation", *Biochemistry*; 1998, pp. 17865-17874, vol. 37, No. 51.

Krapf, F. et al; "Determination of Complement Activating Circulating Immune Complexes and an Example for Antigen Specific Immune Complex Assays", *Journal of Clinical Lab Immunology*; 1986, pp. 183-187, vol. 21.

Kuck, H. et al.; Diagnosis of Occult Subrentinal Neovasculariztion in Age-related Macular Degeneration by Infrared Scanning Laser Videoangiography, *Retina*; 1993, pp. 36-29, vol. 13, No.1.

Kylstra, J.A. et al; Letter to the Journal entitled, "Cone-rod retinal dystrophy in a patient with neurofibromatosis type 1", *Canadian Journal of Ophthalmology*; 1993, pp. 79-80, vol. 28, No. 2.

Langlois, P. et al; "Plasma concentrations of complement-activation complexes correlate with disease activity in patients diagnosed with isolated central nervous system vasculitis", *Journal of Allergy Clinical Immunology*; Jan. 1989, pp. 11-16, vol. 83, No. 1.

Lawn et al; "The Sequence of Human Serum Albumin cDNA and Its Expression in *E. coli*", *Nucleic Acids Research*, 1981, pp. 6103-6114, vol. 9, No. 22.

Li, X. et al.; "A pineal reluatory element (PIRE) mediates transactivation by the pineal/retina-specific transcription factor CRX", *Proc. Natl. Acad. Sci. USA*; 1998, pp. 1876-1881, vol. 95.

Linder, E. et al; "An Immunofluorescence Assay for Complement Activation by the Classical Pathway", *Journal of Immunological Methods*; 1981, pp. 49-59, vol. 47.

Lotery, A.J. et al; "Localisation of a Gene for Central Areolar Choroidal Dystrophy to Chromosome 17p", *Investigative Ophthalmology & Visual Science*; Feb. 15, 1996; pp. 1124, vol. 37, No. 3 (Abstract only).

Lubinski, W. et al; "Foveal electroretinogram-application in diagnosis of macular diseases. Preliminary report.", *Klin Oczna*; 1998, pp. 263-268, vol. 100, No. 5. (Translated abstract of document included).

Lynch, N. et al; "Characterisation of the rat and mouse homologues of gC1qBP, a 33 kDa glycoprotein that binds to the globular 'heads' of C1q". *FEBS Letters*; 1997, pp. 111-114, vol. 418.

Mahant, S., et al.; "Retinal dystrophy in 18q- (de Grouchy) syndrome.", *Am. J. Hum. Genet.*; 1995, p. A96, vol. 57. (Abstract only).

Marmorstein, Alan D., et al; "Bestrophin, the product of the Best vitelliform macular dystrophy gene (*VMD2*), localizes to the basolateral plasma membrane of the retinal pigment epithelium", *PNAS*; Nov. 7, 2000; pp. 12758-12763; vol. 97, No. 23.

Marquardt, A. et al; "Mutations in a novel gene, *VMD2*, encoding a protein of unknown properties cause juvenile onset vitelliform macular dystrophy (Best's disease)", *Human Molecular Genetics*; 1998, pp. 1517-1525, vol. 7, No. 9, Oxford University Press.

Marx; "Testing of Autoimmune Therapy Begins", *Science*, Apr. 1991, pp. 27-28, vol. 252.

Metzler and Wraith; "Inhibition of experimental autoimmune encephalomyelitis by inhalation but not oral administration of the encephalitogenic peptide: influence of MHC binding affinity", *International Immunology*, 1993, pp. 1159-1165, vol. 5, No. 9.

Milis, L. et al; "Vitronectin-mediated inhibition of complement: evidence for different binding sites for C5b-7 and C9", *Clin Exp Immunol.*; 1993, pp. 114-119, vol. 92.

Minh, Do-Quang et al; "Serial complement measurements in patients with leukaemia", *Clin Lab Haematol.*; 1983, pp. 23-34, vol. 5.

Mold, C. et al; "CR2 is a Complement Activator and the Covalent Binding Site for C3 During Alternative Pathway Activation by Raji Cells", *Journal of Immunology*; Mar. 15, 1988; pp. 1923-1929, vol. 140, No. 6.

Mousa, S. et al. "Role of Hypoxia and Extracellular Matrix-Integrin Binding in the Modulation of Angiogenic Growth Factors Secretion by Retinal Pigmented Epithelial Cells", *Journal of Cellular Biochemistry*, 1999, pp. 135-143, vol. 74.

Mullins, R. et al.; "Drusen associated with aging and age-related macular degeneration contain proteins common to extracellular deposits associated with atherosclerosis, elastosis, amyloidosis, and dense deposit disease", *The FASEB Journal*; May 2000, pp. 835-846, vol. 14.

Munroe, P. et al; "Spectrum of Mutations in the Batten Disease Gene, CLN3", *American Journal of Human Genetics*; 1997, pp. 310-316, vol. 61.

Newell, S., et al.; :Hemolytic and antigentic measurements of complement. A comparison of serum and plasma samples in normal individuals and patients; *J Lab Clin Med*; Sep. 1982; pp. 437-444; vol. 100, No. 3.

Ng, Y.C. et al.; "Immune complexes and erythrocyte CR1 (complement receptor type 1): effect of CR1 numbers on binding and release reactions", *Clin Exp Immunol.*; 1988, pp. 481-485, vol. 71.

Padma, T. and Murty, J.S., "Association of Genetic Markers with Some Eye Diseases", *Acta Anthropogenetica*, 1983, pp. 1-12, vol. 7, No. 1.

Payne, A. et al; "A mutation in guanylate cyclase activator 1A (GUCA1A) in an autosomal dominant cone dystrophy pedigree mapping to a new locus on chromosome 6p21.1", *Human Molecular Genetics*; 1998, pp. 273-277, vol. 7 No. 2, Oxford University Press.

Pinter, C. et al; "Presence of autoantibodies against complement regulatory proteins in relapsing-remitting multiple sclerosis", *Journal of Neurovirology*; 2000, pp. S42-S46, vol. 6, Suppl. 2, Macmillan Publishers Ltd.

Quax-Jeuken, Y. et al; "βs-Crystallin: structure and evolution of a distinct member of the βγ-superfamily", *EMBO Journal*; 1985, pp. 2597-2602, vol. 4, No. 10.

Rabb, M. et al, "A North Carolina Macular Dystrophy Phenotype in a Belizean Family Maps to the MCDR1 Locus", *American Journal of Ophthalmology*, Apr. 1998, pp. 502-508, vol. 125, No. 4.

Ratnoff, W. et al.; "Immunohistochemical Localization of C9 Neoantigen and the Terminal Complement Inhibitory Protein CD59 in Human Endometrium", *American Journal of Reproductive Immunology*; 1995, pp. 72-79, vol. 34, Munksgarard, Copenhagen.

Ravelli, A. et al; "IgG autoantibodies to complement C1q in pediatric-onset systemic lupus erythematosus", *Clinical and Experimental Rheumatology*; 1997, pp. 215-219, vol. 15.

Reaven, Peter; "Mechanisms of Atherosclerosis: Role of LDL Oxidation", *Free Radicals in Diagnostic Medicine*, 1994, pp. 113-128, Plenum Press, New York, U.S.A.

Rodrick, M. et al; "An Evaluation of Two Antigen Nonspecific Assays for Circulating Immune Complexes Using an Model System", *J. Clin Lab Immunol*; 1982, pp. 193-198, vol. 7, No. 3.

Sacks, J.G, et al; "The Pathogenesis of Optic Nerve Drusen", *Archives of Ophthalmology*, Mar. 1997, pp. 425-428, vol. 95, No. 3.

Seymour, A. et al; "Linkage Analysis of X-linked Cone-Rod Dystrophy: Localization to Xp11.4 and Definition of a Locus Distinct from RP2 and RP3", *Am. J. Hum. Genet.*; 1998, pp. 122-129, vol. 62.

Slingsby, C. and Bateman, O.A.; "Rapid Separation of Bovine β-Crystallin Subunits βB1, βB2, βB3, and βA4", *Exp Eye Res*; 1990, pp. 21-26, vol. 51.

Small, K. et al.; "Mapping of Autosomal Dominant Cone Degeneration to Chromosome 17p", *American Journal of Ophthalmology*; 1996, pp. 13-18, vol. 121, No. 1.

Spraul, et al; "Optical Coherence Tomography of Age-Related Macular Degeneration. Correlation of Diagnostic Techniques of Fluorescence angiography and OCT" (title translated) *Klin Monatsbl Augenheilkd*; Mar. 1998, pp. 141-148, vol. 212.

Stone, Edwin M., et al., "A single *EFEMP1* mutation associated with both Malattia Leventinese and Doyne honeycomb retinal dystrophy"; *Nature Genetics*; Jun. 1999; pp. 199-202; vol. 22.

Strife, C. et al; "Autoantibody to complement neoantigens in membranoproliferative glomerulonephritis", *The Journal of Pediatrics*; May 1990, pp. S98-S102, vol. 116, No. 5.

Suzuki et al.; "Complete amino acid sequence of human vitronectin deduced from cDNA. Similarity of cell attachment sites in vitronectin and fibronectin", *EMBO J*, 1985, pp. 2519-2524, vol. 4, No. 10.

Tanaka, S. et al; "Assay of classical and alternatie pathway activities of murine complement using antibody-sensitized rabbit erythrocytes", *Journal of Immunological Methods*; 1986, pp. 161-170, vol. 86, Elsevier Science Publishers B.V.

Thomson et al; "Microchimerism, Dendritic Cell Progenitors and Transplantation Tolerance", *Stem Cells*; 1995, pp. 622-639, vol. 13.

Tomimori-Yamashita, J. et al; "Antibody-based enzyme-linked immunosorbent assay for determination of anti-PGL-I specific circulating immune complex in leprosy patients.", *Lepr Rev*; 1999, pp. 261-271, vol. 70.

Tran, H. et al.; "Human Fibulin-1D: Molecular Cloning, Expression and Similarity with S1-5 Protein, a New Member of the Fibulin Gene Family", *Matrix Biology*, 1997, pp. 479-493, vol. 15.

Trentham et al; "Effects of Oral Administration of Type II Collagen on Rheumatoid Arthritis", *Science*; 1993, pp. 1727-1730, vol. 261.

Tschopp, J et al.; "Clusterin, the Human Apolipoprotein and Complement Inhibitor, Binds to Coplement C7, C8β, and the b Domain C9", *Journal of Immunology*.; Aug. 15, 1993; pp. 2159-2165, vol. 151, No. 4, Printed in the U.S.A.

Van Dijk, H. et al.; "Determination of Alternative Pathway of Complement Activity in Mouse Serum Using Rabbit Erythrocytes", *Journal of Immunolical Methods*; 1890, pp. 29-39, vol. 36, Elsevier/North-Holland Biomedical Press.

Volanakis, J.; C-Reactive Protein and the Plasma Protein Response to Tissue Injury. Part IV. Biological Properties and Function of CRP and SAP: "Complement Activation by C-Reactive Protein Complexes", *Annals of the New York Academy of Sciences*; 1982, pp. 235-250, vol. 389.

Warburg, M., et al; "Deletion Mapping of a Retinal Cone-Rod Dystrophy: Assignment to 18q211", *American Journal of Medical Genetics*; 1991, pp. 288-293, vol. 39.

Wexler et al; "Primary amino acid sequence and structure of human pyruvate carboxylase", *Biochimica et Biophysica Acta*, 1994, pp. 46-52, vol. 1227.

Yamanaka, R. et al; "CCAAT/enhancer binding protein ε is preferentially up-regulated during granulocytic differentiation and its functional versatility is determined by alternative use of promoters and differential splicing.", *Proc Natl Acad Sci USA*; Jun. 1997, pp. 6462-6467, vol. 94.

Yuzawa, M. et al; "Clinical evaluation of indocyanine green videoangiography in the diagnosis of choroidal neovascular membrane associated with age-related macular degeneration", *European Journal of Ophthalmology*; 1992, pp. 115-121, vol. 2, No. 3.

Zhang, K. et al; "A dominant Stargardt's Macular Dystrophy Locus Maps to Chromosome 13q34", *Arch. Ophthalmol.*; Jun. 1994, pp. 759-764, vol. 112.

Zhang, Y, et al; "Lysis via the lectin pathway of complement activation: minireview and lectin pathway enhancement of endotoxin-initiated hemolysis"; *Immunopharmacology*; May 1999; pp. 81-90; vol. 42.

\* cited by examiner

DIAGNOSTICS AND THERAPEUTICS FOR MACULAR DEGENERATION-RELATED DISORDERS

CROSS-REFERENCE TO RELATED APPLICATIONS

This application is a continuation of U.S. patent application Ser. No. 10/084,639 (filed Feb. 25, 2002), issued as U.S. Pat. No. 7,011,952, which is a continuation-in-part of U.S. patent application Ser. No. 09/845,745 (filed Apr. 30, 2001), now abandoned, which is continuation-in-part of U.S. patent application Ser. No. 09/510,230 (filed Feb. 22, 2000) now abandoned, and also claims priority to U.S. Provisional Application No. 60/200,698 (filed Apr. 29, 2000). The full disclosures of these applications are incorporated herein by reference in their entirety for all purposes.

FIELD OF THE INVENTION

The invention relates in general to diagnostics for macular degeneration-related disorders or diseases. The invention finds application in the biomedical sciences.

BACKGROUND OF THE INVENTION

Macular degeneration is a clinical term that is used to describe a family of diseases that are all characterized by a progressive loss of central vision associated with abnormalities of Bruch's membrane, the choroid, the neural retina and/or the retinal pigment epithelium. These disorders include very common conditions that affect older subjects (age-related macular degeneration or AMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

Age-related macular degeneration (AMD), the most prevalent macular degeneration, is associated with progressive diminution of visual acuity in the central portion of the visual field, changes in color vision, and abnormal dark adaptation and sensitivity. Two principal clinical manifestations of AMD have been described as the dry, or atrophic, form, and the wet, or exudative, form. The most significant risk factor for the development of both forms are age and the deposition of drusen, abnormal extracellular deposits, behind the retinal pigment epithelium (RPE). Drusen causes a lateral stretching of the RPE monolayer and physical displacement of the RPE from its immediate vascular supply, the choriocapillaris. This displacement creates a physical barrier that may impede normal metabolite and waste diffusion between the choriocapillaris and the retina.

Malattia Leventinese (ML), also termed Doyne's honeycomb choroiditis or dominant drusen, is a genetic, early onset form of macular degeneration characterized by numerous, often confluent drusen that may radiate peripherally from the macula. This disease is phenotypically similar to age-related macular degeneration (AMD). The occurrence of sub-RPE deposits in ML make it a valuable model for understanding pathways that participate in age-related macular degeneration (AMD).

SUMMARY OF THE INVENTION

In one aspect, the present invention provides methods for diagnosing, or identifying a predisposition to the development of, a macular degeneration-related disorder in a subject. The methods comprise detecting in a biological sample from the subject the presence or an abnormal level of an autoantibody against, or an immune complex containing, at least one macular degeneration-associated molecule. The macular degeneration-associated molecule is selected from the group consisting of fibulin-3, vitronectin, β crystallin A2, β crystallin A3, β crystallin A4, β crystallin S, glucose-regulated protein 78 kD (GRP-78), calreticulin, 14-3-3 protein epsilon, serotransferrin, albumin, keratin, pyruvate carboxylase, villin 2, and complement 1q binding protein/hyaluronic acid binding protein ("complement 1q component").

In some methods, the detecting step entails contacting autoantibodies in the biological sample with the macular degeneration-associated molecule (or an antigenic fragment), and detecting a specific interaction between the autoantibody and the macular degeneration-associated molecule (or an antigenic fragment). In some of these methods, there is a further step of precipitating a complex formed between the autoantibody and the macular degeneration-associated molecule before the detecting step. In some other methods, the detecting step entails precipitating a naturally occurring immune complex from the biological sample. All of these methods can further comprise detecting a level of the autoantibody or the naturally occurring immune complex in a control subject and comparing levels of obtained from the subject and the control subject. The biological sample can be a lymph fluid, eye fluid, urine, blood plasma, serum, or whole blood from the subject. or isolating a naturally occurring immune complex. Some methods comprise a further step of contacting the biological sample with a labeled antibody that competes with the autoantibody to form complexes with the macular degeneration-associated molecule. In some methods, the macular degeneration-associated molecule (or an antigenic fragment) is bound to a solid phase. Such methods further comprise a step of removing the solid phase from the serum sample to separate the complexes from unbound, labeled antibody.

Some methods of the invention are specifically for the diagnosis of Malattia Leventinese. In some of these methods, the macular degeneration-associated molecule is selected from the group consisting of fibulin 3, β crystallin A2, β crystallin A3, β crystallin A4, β crystallin S, glucose-regulated protein 78 kD (GRP-78), complement 1q binding protein/hyaluronic acid binding protein, calreticulin, 14-3-3 protein epsilon, serotransferrin, albumin, keratin, pyruvate carboxylase, and villin 2. Some other methods of the invention are specifically for the diagnosis of age-related macular degeneration. In some of such methods, the macular degeneration-associated molecule is vitronectin.

Some methods of the invention further comprise detecting at least one macular degeneration-associated genetic marker, drusen-associated phenotypic marker, or drusen-associated genotypic marker in the subject. Some methods further comprise examining the subject with an ophthalmologic procedure.

In one aspect, the invention provides methods for treating a macular degeneration-related disorder in a subject. Such methods comprise inducing immune tolerance to at least one macular degeneration-associated molecule in the subject. The macular degeneration-associated molecule is selected from the group consisting of fibulin 3, β crystallin A2, β crystallin A3, β crystallin A4, β crystallin S, glucose-regulated protein 78 kD (GRP-78), calreticulin, hyaluronan-binding protein, 14-3-3 protein epsilon, serotransferrin, albumin, keratin, pyruvate carboxylase, and villin 2.

In another aspect, the invention provides methods for identifying genes that cause macular degeneration-related disorders. The methods comprise detecting an autoantibody against, or an immune complex containing, an autoantigen that is encoded by a gene that causes a macular degeneration-related disorder. In some methods, the macular degeneration-related disorder is AMD.

In still another aspect, the present invention provides kits for diagnosing or identifying a predisposition to the development of a macular degeneration-related disorder in a subject. The kits comprise at least one macular degeneration-associated molecule (or an antigenic fragment), a solid support to which is bound the macular degeneration-associated molecule (or its antigenic fragment), and a binding molecule that is capable of specifically binding to a human antibody. Some of the kits are specifically provided for the diagnosis of Malattia Leventinese or age-related macular degeneration.

DETAILED DESCRIPTION

The present invention is predicated in part on the discovery that autoantibodies against various macular degeneration-associated molecules (e.g., fibulin 3 and vitronectin) are present in patients with macular degeneration-related disorders (e.g., Malattia Leventinese or AMD). Thus, presence or abnormal levels of such autoantibodies in a biological sample from a subject can be indicative of the existence of, or a predisposition to developing, various macular degeneration-related disorders. In accordance with the discovery, the present invention provides methods for diagnosing, or determining a predisposition to development of, a macular degeneration-related disorder by detecting the presence or an abnormal levels of autoantibodies against macular degeneration-associated molecules (e.g., fibulin-3, vitronectin). The disorders or disease that can be diagnosed with the methods include, e.g., age-related macular disorder (AMD), North Carolina macular dystrophy, Sorsby's fundus dystrophy, Stargardt's disease, pattern dystrophy, Best disease, dominant drusen, and Malattia Leventinese. Other ocular diseases that can be diagnosed or treated with the methods include, e.g., retinal detachment, chorioretinal degenerations, retinal degenerations, photoreceptor degenerations, RPE degenerations, mucopolysaccharidoses, rod-cone dystrophies, cone-rod dystrophies, and cone degenerations.

The methods are suitable for large scale screening of a population of subjects for the presence of these macular degeneration-related disorders, optionally, in conjunction with additional biochemical and/or genetic markers of other disorders that may reside in the subjects. The methods are also suitable for monitoring subjects who have previously been diagnosed with a macular degeneration-related disorder, particularly their response to treatment. The methods of detecting the presence or abnormal levels of autoantibodies against several macular degeneration-associated molecules can be performed in combination, optionally in further combination with detecting other genetic, phenotypic, or genotypic markers correlated with macular degeneration-related disorders or drusen-associated diseases, as described by WO 00/52479. Optionally, analysis of phenotypic markers can be combined with polymorphic analysis of genes encoding the macular degeneration-associated molecules for polymorphisms correlated with the macular degeneration-related disorders.

The following sections provide guidance for making and using the compositions of the invention, and for carrying out the methods of the invention.

I Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the preferred methods and materials are described. The following definitions are provided to assist the reader in the practice of the invention.

The term "agent" includes any substance, molecule, element, compound, entity, or a combination thereof. It includes, but is not limited to, e.g., protein, oligopeptide, small organic molecule, polysaccharide, and polynucleotide. It can be a natural product, a synthetic compound, or a chemical compound, or a combination of two or more substances. Unless otherwise specified, the terms "agent", "substance", and "compound" can be used interchangeably.

The term "agonist" is an agent that enhances or upregulates (e.g., potentiates or supplements) the production or activity of a gene product. An agonist can also be a compound which increases the interaction of a gene product, molecule or cell with another gene product, molecule or cell, e.g., of a gene product with another homologous or heterologous gene product, or of a gene product with its receptor. A preferred agonist is a compound which enhances or increases binding or activation of a transcription factor to an upstream region of a gene and thereby activates the gene. Any agent that activates gene expression, e.g., by increasing RNA or protein synthesis or decreasing RNA or protein turnover, or gene product activity may be an agonist whether the agent acts directly on the gene or gene product or acts indirectly, e.g., upstream in the gene regulation pathway. Agonists may be RNAs, peptides, antibodies and small molecules, or a combination thereof.

The term "antagonist" is an agent that downregulates (e.g., suppresses or inhibits) the production or activity of a gene product. Such an antagonist can be an agent which inhibits or decreases the interaction between a gene product, molecule or cell and another gene product, molecule or cell. A preferred antagonist is a compound which inhibits or decreases binding or activation of a transcription factor to an upstream region of a gene and thereby blocks activation of the gene. Any agent that inhibits gene expression or gene product activity may be an antagonist whether the agent acts directly on the gene or gene product or acts indirectly, e.g., upstream in the gene regulation pathway. An antagonist can also be a compound that downregulates expression of a gene or which reduces the amount of gene product present, e.g., by decreasing RNA or protein synthesis or increasing RNA or protein turnover. Antagonists may be RNAs, peptides, antibodies and small molecules, or a combination thereof.

The term "antibody" or "immunoglobulin" is used to include intact antibodies and binding fragments thereof. Typically, fragments compete with the intact antibody from which they were derived for specific binding to an antigen fragments including separate heavy chains, light chains Fab, Fab', F(ab')2, Fabc, and Fv. Fragments are produced by recombinant DNA techniques, or by enzymatic or chemical separation of intact immunoglobulins. The term "antibody" also includes one or more immunoglobulin chain that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "antigenic fragment" of a macular degeneration-associated molecule (e.g., fibulin 3 or vitronectin) refers to a portion of the molecule that comprises at least 8, 12, 15, 20, 50, 100, or more contiguous amino acid residues of the molecule.

The term "antisense molecules" include antisense or sense oligonucleotides comprising a single-stranded nucleic acid sequence (either RNA or DNA) capable of binding to target mRNA (sense) or DNA (antisense) sequences for a specific protein (e.g., a complement pathway molecule). The ability to derive an antisense or a sense oligonucleotide, based upon a cDNA sequence encoding a given protein is described in, e.g., Stein and Cohen (Cancer Res. 48:2659, 1988) and van der Krol et al. (BioTechniques 6:958, 1988).

The term "binding molecule" when used to refer to the detection of a human autoantibody refers to a molecule that specifically binds to a class of antibodies, e.g., protein A, protein G, a goat anti-immunoglobulin antibody, or the equivalent.

The term "complement activity" broadly encompasses the biochemical and physiological activities associated with the complement system, individual complement pathway associated molecules, as well as genes encoding these molecules. Therefore, complement activities include, e.g., structure and expression of a gene encoding a complement pathway molecule, biochemical activity (e.g., enzymatic or regulatory) of a complement pathway molecule, cellular activities that initiate or result from activation of the complement system, and presence of serum autoantibodies against complement pathway molecules.

The terms "complement pathway associated molecules," "complement pathway molecules," and "complement pathway associated proteins" are used interchangeably and refer to the various molecules that play a role in complement activation and the downstream cellular activities mediated by, responsive to, or triggered by the activated complement system. They include initiators of complement pathways (i.e., molecules that directly or indirectly triggers the activation of complement system), molecules that are produced or play a role during complement activation (e.g., complement proteins/enzymes such as C3, C5, C5b-9, Factor B, MASP-1, and MASP-2), complement receptors or inhibitors (e.g., clusterin, vitronectin, CR1, or CD59), and molecules regulated or triggered by the activated complement system (e.g., membrane attack complex-inhibitory factor, MACIF; see, e.g., Sugita et al., J Biochem, 106:589-92, 1989). Thus, in addition to complement proteins noted above, complement pathway associated molecules also include, e.g., C3/C5 convertase regulators (RCA) such as complement receptor type 1 (also termed CR1 or CD35), complement receptor type 2 (also termed CR2 or CD21), membrane cofactor protein (MCP or CD46), and C4bBP; MAC regulators such as vitronectin, clusterin (also termed "SP40,40"), CRP, CD59, and homologous restriction factor (HRF); immunoglobulin chains such as Ig kappa, Ig lambda, or Ig gamma; C1 inhibitor; and other proteins such as CR3, CR4 (CD11b/18), and DAF (CD 55).

A "detectable label" refers to an atom (e.g., radionuclide), molecule (e.g., fluorescein), or complex, that is or can be used to detect (e.g., due to a physical or chemical property) the presence of another molecule. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical, and chemical means.

The term "drusen" refers to deposits that accumulate between the RPE basal lamina and the inner collagenous layer of Bruch's membrane (see, e.g., van der Schaft et al., Ophthalmol. 99: 278-86, 1992; Spraul et al. Arch. Ophthalmol. 115: 267-73, 1997; and Mullins et al., *Histochemical comparison of ocular "drusen" in monkey and human*, In M. LaVail, J. Hollyfield, and R. Anderson (Eds.), in *Degenerative Retinal Diseases* (pp. 1-10). New York: Plenum Press, 1997).

The term "drusen-associated disease," or "drusen-associated disorder," refers to any disease in which formation of drusen or drusen-like extracellular disease plaque takes place, and for which drusen or drusen-like extracellular disease plaque causes or contributes thereto or represent a sign thereof. Drusen-associated disease or disorder primarily includes macular degeneration-related disorders wherein drusen is present. But it also encompasses non-ocular age-related diseases with extracellular disease plaques such as amyloidosis, elastosis, dense deposit disease, and/or atherosclerosis. The term also includes glomerulonephritis (e.g., membranous and post-streptococcal/segmental which have associated ocular drusen).

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

The term "fusion protein" refers to a composite polypeptide, i.e., a single contiguous amino acid sequence, made up of two (or more) distinct, heterologous polypeptides which are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous polypeptide, or by chemical synthesis methods well known in the art.

The term "immune complex" refers to a complex formed between an antibody and its cognate antigen (e.g., a macular degeneration associated molecule) as a result of the binding affinity of the antibody for the antigen, or between a binding partner and its cognate antibody as a result of the binding affinity of the binding partner for the antibody.

The term "macular degeneration-related disorder" refers to any of a number of conditions in which the retinal macula degenerates or becomes dysfunctional, e.g., as a consequence of decreased growth of cells of the macula, increased death or rearrangement of the cells of the macula (e.g., RPE cells), loss of normal biological function, or a combination of these events. Macular degeneration results in the loss of integrity of the histoarchitecture of the cells and/or extracellular matrix of the normal macula and/or the loss of function of the cells of the macula. Examples of macular degeneration-related disorder include AMD, North Carolina macular dystrophy, Sorsby's fundus dystrophy, Stargardt's disease, pattern dystrophy, Best disease, dominant drusen, and Malattia Leventinese (radial drusen). The term also encompasses extramacular changes that occur prior to, or following dysfunction and/or degeneration of the macula. Thus, the term "macular degeneration-related disorder" also broadly includes any condition which alters or damages the integrity or function of the macula (e.g., damage to the RPE or Bruch's membrane). For example, the term encompasses retinal detachment, chorioretinal degenerations, retinal degenerations, photoreceptor degenerations, RPE degenerations, mucopolysaccharidoses, rod-cone dystrophies, cone-rod dystrophies and cone degenerations.

The term "macular degeneration-associated molecule" broadly refer to a large spectrum of proteins, peptides, compounds, or complexes that are involved or implicated in the development and etiology of various macular degeneration-related disorders. For example, it includes complement pathway associated molecules and drusen associated markers as described in commonly assigned U.S. patent application Ser. Nos. 09/845,745 and 09/510,230. The term also includes the product of an abnormal gene (e.g., a mutated gene or disease-causing gene) which causes a macular degeneration related disorder (e.g., AMD or Malattia Leventinese). In the context of detecting an autoantibody in a subject, macular degeneration-associated molecule refers to macular degeneration-associated polypeptides or macular degeneration-associated antigens autoantibodies against which are present in patients with macular degeneration-related disorders (AMD or Malattia Leventinese). Thus, this term encompasses molecules such as fibulin-3, vitronectin, β crystallin A2, β crystallin A3, β crystallin A4, β crystallin S, glucose-regulated protein 78 kD (GRP-78), complement 1q binding protein/hyaluronic acid binding protein (or hyaluronan-binding protein), calreticulin, 14-3-3 protein epsilon, serotransferrin, albumin, keratin, pyruvate carboxylase, and villin 2. It also includes antigenic fragments of these molecules.

The terms "modulation", "alteration", "modulate", or "alter" are used interchangeably herein to refer to both upregulation (i.e., activation or stimulation (e.g., by agonizing or potentiating) and downregulation (i.e., inhibition or suppression (e.g., by antagonizing, decreasing or inhibiting)) of an activity or a biological process (e.g., complement process). "Modulates" or "alters" is intended to describe both the upregulation or downregulation of a process. A process which is upregulated by a certain stimulant can be inhibited by an antagonist to that stimulant. Conversely, a process that is downregulated by a certain stimulant can be inhibited by an antagonist to that stimulant.

By "randomized" is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized proteinaceous test agents. The library can be fully randomized, with no sequence preferences or constants at any position.

"Specific binding" between two entities means an affinity of at least $10^6$, $10^7$, $10^8$, $10^9$ M–1, or $10^{10}$ M–1. Affinities greater than $10^8$ M–1 are preferred.

A "subject" includes both humans and other animals (particularly mammals) and other organisms that receive either prophylactic or therapeutic treatment.

The term "test agent" as used herein describes any molecule, e.g., protein, oligopeptide, small organic molecule, polysaccharide, polynucleotide, etc., that can be screened for their capability of directly or indirectly altering the bioactivities of a complement pathway molecule.

A "variant" refers to a polypeptide amino acid sequence that is altered by one or more amino acid residues relative to the wild type sequence, or a polynucleotide sequence that is altered by one or more nucleotide residue relative to the wild type sequence. A variant can be an allelic variant, a species variant, or an induced variant. The variant can have "conservative" changes, wherein a substituted amino acid has similar structural or chemical properties (e.g., replacement of leucine with isoleucine). Alternatively, a variant can have "nonconservative" changes (e.g., replacement of glycine with tryptophan). Analogous minor variations can also include amino acid deletions or insertions, or both. Guidance in determining which amino acid residues can be substituted, inserted, or deleted without abolishing biological or immunological activity can be found using computer programs well known in the art, for example, LASERGENE™ software.

II. Diagnosing: Detecting Autoantibodies or Immune Complexes

The present invention provides methods for diagnosing, or determining a predisposition to development of, a macular degeneration-related disorder by detecting the presence or abnormal levels of at least one autoantibody against, or immune complexes containing, macular degeneration-associated molecules in a biological sample from a subject. The autoantibodies to be detected with methods of the present invention include antibodies that specifically bind to any macular degeneration-associated molecules, e.g., fibulin-3, vitronectin, β crystallin A2, β crystallin A3, β crystallin A4, β crystallin S, calreticulin, 14-3-3 protein epsilon, serotransferrin, albumin, keratin, pyruvate carboxylase, or villin 2.

A. General Consideration

Typically, a diagnostic test works by comparing a measured level of at least one marker (e.g., an autoantibody against a macular degeneration-associated molecule) in a subject with a baseline level (which can be zero) determined in a control population of subjects unaffected by a macular degeneration-related disorder. If the measured level does not differ significantly from baseline levels in a control population, the outcome of the diagnostic test is considered negative. On the other hand, if there is a significant departure between the measured level in a subject and baseline levels in unaffected subjects, it signals a positive outcome of the diagnostic test, and the subject is considered to have abnormal presence or an abnormal level of that marker.

A departure is considered significant if the measured value falls outside the range typically observed in unaffected subjects due to inherent variation between subjects and experimental error. For example, in some methods, a departure can be considered significant if a measured level does not fall within the mean plus one standard deviation of levels in a control population. Typically, a significant departure occurs if the difference between the measured level and baseline levels is at least 20%, 30%, or 40%. Preferably, the difference is by at least 50% or 60%. More preferably, the difference is more than at least 70% or 80%. Most preferably, the difference is by at least 90%. The extent of departure between a measured value and a baseline value in a control population also provides an indicator of the probable accuracy of the diagnosis, and/or of the severity of the disease being suffered by the subject.

Various biological samples from a subject can be used for the detection, e.g., samples obtained from any organ, tissue, or cells, as well as blood, urine, or other bodily fluids (e.g., eye fluid). For some diagnostic methods, a preferred sample is eye fluid. For some other methods, a preferred tissue sample is whole blood and products derived therefrom, such as plasma and serum. The sample can also be an eye tissue biopsy obtained during surgery. Other sources samples are skin, hair, urine, saliva, semen, feces, sweat, milk, amniotic fluid, liver, heart, muscle, kidney and other body organs. Tissue samples are typically lysed to release the protein and/or nucleic acid content of cells within the samples. The protein or nucleic acid fraction from such crude lysates can then be subject to partial or complete purification before analysis.

In some methods, the autoantibodies are detected by demonstrating specific binding to a full length macular degeneration-associated molecule. In some methods, an antigenic fragment of the macular degeneration-associated molecule is employed. In some methods, the macular degeneration-associated molecule or an antigenic fragment is immobilized on a support, such as a bead, plate or slide (e.g., as described in U.S. Pat. No. 5,741,654), and contacted with the biological sample suspected of containing an autoantibody in a liquid phase (e.g., a liquid sample or a tissue sample lysate). In some methods, various macular degeneration-associated molecules or their antigenic fragments are presented on a solid support (e.g., on a polyacrylamide gel separated by electrophoresis) and then contacted with a biological sample to identify specific binding to the molecules.

The presence or an abnormal level of an autoantibody in a biological sample can be detected with various immunological methods. For example, radioimmunoassay, immunofluorescence assay, enzyme-linked immunosorbent assay (ELISA), immunocytochemical assay, and immunoblotting can all be used to detect antibody-antigen reaction.

In some methods, multiple diagnostic tests for multiple markers (e.g., multiple autoantibodies or other macular degeneration-related markers as described in application Ser. No. 09/845,745) are performed on the same subject. Typically, multiple tests are performed on different aliquots of the same biological sample. However, multiple assays can also be performed on separate samples from the same tissue source, or on multiple samples from different tissue sources. For example, a test for one marker can be performed on a plasma sample, and a test for a second marker on a whole blood sample. In some methods, multiple samples are obtained from the same subject at different time points. In such methods, the multiple samples are typically from the same tissue, for example, all serum.

B. Detecting Autoantibodies Against or Immune Complexes Containing Macular-degeneration-associated Molecules The present invention provide methods for diagnosing the presence or a predisposition to the development of a macular degeneration related disorder by detecting autoantibodies against, or immune complexes containing, macular degeneration-associated molecules in a biological sample from a subject. As discussed above, any antibody-containing biological sample can be collected from the subject and employed in carrying out the present invention, including, e.g., blood, blood serum, blood plasma, eye fluid, urine, lymph fluid, or eye tissue.

Various macular degeneration-associated molecules or their antigenic fragments can be employed in the methods of the present invention. Preferably, the following molecules or their antigenic fragments are employed: fibulin-3, vitronectin, β crystallin A2, β crystallin A3, β crystallin A4, β crystallin S, glucose-regulated protein 78 kD (GRP-78), calreticulin, hyaluronan-binding protein, 14-3-3 protein epsilon, serotransferrin, albumin, keratin, pyruvate carboxylase, and villin 2. Biochemical properties of these macular degeneration-associated molecules have been characterized in the literature, and their nucleotide and amino acid sequences have been disclosed in the art. See, e.g., fibulin 3 (also known as protein S1-5; see Tran et al., Matrix Biol, 15:479-93, 1997; and Giltay et al., Matrix Biol, 18:469-80, 1999); vitronectin (Suzuki et al., EMBO J, 4:2519-24, 1985); β crystallin A2, A3, and A4 (Slingsby et al., Exp Eye Res, 51:21-6, 1990); β crystallin S (Quax-Jeuken et al., EMBO J, 4:2597-602, 1985); glucose-regulated protein 78 kD (Kiang et al., Chin J Physiol, 40:213-9, 1997); calreticulin (Kovacs et al., Biochemistry, 37:17865-74, 1998); hyaluronan-binding protein (Lynch et al., FEBS Lett, 418: 111-4, 1997); 14-3-3 protein epsilon (Yamanaka et al., Proc Natl Acad Sci USA, 94:6462-7, 1997); serotransferrin (Campbell et al., J Biol Chem, 252:5996-6001, 1977); human albumin (Lawn et al., Nucleic Acids Res, 9:6103-114, 1981); keratin (Hintner et al., J Invest Dermatol, 93:656-61, 1989); pyruvate carboxylases (Wexler et al., Biochim Biophys Acta, 1227:46-52, 1994); and villin 2 (Burgess et al., J. Immunol., 149: 1847-1852, 1992; and U.S. Pat. No. 5,773,573). These molecules can be obtained from various commercial suppliers. Alternatively, these molecules or their antigenic fragments can be readily produced with molecular biological and biochemical techniques, e.g., by recombinant production using an expression vector that encodes a macular degeneration-related polypeptide or an antigenic fragment (Sambrook et al., Molecular Cloning A Laboratory Manual, 3rd Ed., 2000, Cold Spring Harbor Laboratory Press).

For detection of autoantibodies against macular degeneration-associated molecules in a biological sample in the present invention, a number of routinely practiced immunological methods can be employed. See generally, E. Maggio, Enzyme-Immunoassay, (1980)(CRC Press, Inc., Boca Raton, Fla.); R. Nakamura et al., Enzyme Immunoassays: Heterogeneous and Homogeneous Systems, In Handbook of Experimental Immunology, Vol. 1, chap. 27 (D. M. Weir ed. 1986)(Blackwell Scientific Publications); and U.S. Pat. Nos. 5,814,461, 5,846,740, 5,993,818, 6,121,004, and 6,225,442. Exemplary methods for detecting the presence of an autoantibody in a sample include (1) aggregation reaction (antigens are spread on the surface of blood cells or gelatin powders to which is added a biological sample; an antigen-antibody reaction occurs which allows formation of an aggregation clot) and (2) DID, double immune diffusion method (an extract solution containing antigens and a sample are diffused in a gelatin gel and allow a precipitation reaction).

In addition to detecting the presence of autoantibodies in a sample, many methods can be used to quantitatively measure the levels of the autoantibodies. In some methods, the antigen reacts with the autoantibody in a liquid phase, and the autoantibodies are quantitatively measured by an immunoprecipitation technique. For example, a macular degeneration-related polypeptide (i.e., full length molecules or antigenic fragments) can be detectably labeled (e.g., with an isotope or an enzyme). The polypeptides can be labeled during synthesis (e.g., by adding $^{35}$S-methionine to an in vitro translation system or cellular expression system) or after synthesis. The detectably antigen is added directly to a liquid biological sample (e.g., a serum) to form immune complexes. The immune complexes can be precipitated with polyethylene glycol. The immune complexes can also be isolated with a secondary antibody (e.g., goat anti-human immunoglobulin) or other kind of binding molecules (e.g., protein A or protein G) that is bound to a solid support (e.g., agarose or sepharose beads). The immunoprecipitates are washed several times after being separated from the liquid sample and examined for intensity of the detectable label (e.g., radioactivity). Any autoantibody present in the sample can thus be detected and quantified. Optionally, an unlabelled polypeptide can also be added to compete with the labeled polypeptide for binding to autoantibodies.

In some other methods, assays rely on heterogeneous protocols where the antigen is bound to a solid phase. The antigen (i.e., a macular degeneration-associated molecule or fragment) can be conveniently immobilized on a variety of solid phases, such as dipsticks, particulates, microspheres, magnetic particles, test tubes, microtiter wells, and nitrocellulose or nylon membranes (as described, e.g., in U.S. Pat. No. 5,801,064). Other than being immobilized through a chemical bonding to a solid support, the antigens can also be provided on a solid support, e.g., by polyacrylamide electrophoresis gel as described in the Examples. The solid phase or support is exposed to a liquid biological sample (e.g., a serum) so that the autoantibody, if any, is captured by the antigen on the solid support. By removing the solid phase from the serum sample, the captured autoantibody is removed from unbound autoantibodies and other contaminants in the sample.

The captured autoantibody can then be detected using the non-competitive "sandwich" technique where labeled ligand for the autoantibody is exposed to the washed solid phase. Alternatively, competitive formats rely on the prior introduction of a labeled antibody to the sample so that labeled and unlabelled forms compete for binding to the solid phase. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Enzyme-linked immunosorbent assay (ELISA) methods are described in detail in U.S. Pat. Nos. 3,791,932; 3,839,153; 3,850,752; 3,879,262; and 4,034,074. ELISA assays detect very low titers of autoantibodies.

Autoantibodies can also be detected by solid-phase radioimmunoassay (RIA). The solid phase is exposed to the serum sample in the presence of radio-labeled antibodies that compete for binding to the immobilized ligand. In this assay, the amount of radiolabel bound to the solid phase is inversely related to the amount of autoantibodies initially present in the serum sample. After separation of the solid phase, non-specifically bound radiolabel is removed by washing, and the amount of radiolabel bound to the solid phase determined. The amount of bound radiolabel is, in turn, related to the amount of autoantibodies initially present in the sample.

In some methods, in addition to detecting autoantibodies against macular degeneration-associated autoantigens such as fibulin-3, vitronectin, β crystallin, calreticulin, serotransferrin, keratin, pyruvate carboxylase, C1, and villin 2, the diagnosis also entails examination for specific binding to other autoantigens from the ocular tissues (e.g., RPE, choroid) using proteins extracted from the ocular tissues. For example, proteins extracted from ocular tissues from non-human animals (e.g., rat) or from deceased human beings can be used to screen for autoantibodies against ocular autoantigens in a serum from the subject (see, e.g., Example 3). Detection of autoantibodies against autoantigens from other tissues can be indicative of a systemic nature of that macular degeneration-related disorder.

The diagnostic methods of the present invention are also directed to detecting in a subject circulating immune complexes formed between a macular degeneration-related autoantigen and an autoantibody. The methods discussed above can be readily modified for detection of such immune complexes. For example, an immobilized binding molecule (e.g., protein A or protein G bound to a bead) can be added to a liquid biological sample. After separation from the liquid phase, immune complexes captured by the binding molecules can be analyzed with SDS-PAGE and probed with various antibodies against known macular degeneration-associated molecules (e.g., antibodies against fibulin 3 or vitronectin). The captured antigens can also be subject to direct amino acid sequence analysis. Identity of the immune complexes can thus be revealed.

Presence of such immune complexes in a subject can be indicative of a macular degeneration-related disorder. Significance of circulating immune complexes are well documented in the art. For example, the causative mechanism for glomerulonephritis is typically the deposit of circulating immune complexes in the kidney (see, e.g., U.S. Pat. No. 6,074,642). Circulating immune complexes as a result of activation and consumption of individual complement components have also been shown in many other human diseases occurs (see, e.g., U.S. Pat. No. 5,221,616). Detection of circulating immune complexes also can be of diagnostic value in macular degeneration related disorders. A number of assays are routinely practiced to detect circulating immune complexes in a subject, e.g., as described in Tomimori-Yamashita et al., Lepr Rev, 70(3):261-71, 1999 (antibody-based enzyme-linked immunosorbent assay); Krapf et al., J Clin Lab Immunol, 21(4):183-7, 1986 (fluorescence linked immunosorbent assay); Kazeem et al., East Afr Med J, 67(6):396-403, 1990 (laser immunonephelometry); and Rodrick et al., J Clin Lab Immunol, 7(3):193-8, 1982 (Protein A-glass fiber filter assay, PA-GFF, and polyethylene glycol insolubilization assay). Each of these well known assays can be employed to detect circulating immune complexes for the methods of the present invention.

III. Additional Diagnostic Tests

If a diagnostic test described above gives a positive outcome, the subject is, at minimum, identified as being susceptible to or at risk of a macular degeneration-related disorder (e.g., AMD or ML). The subject is then typically subject to further tests or screening. The additional tests or screening can include examination of the function or physical integrity of an ocular tissue of the subject's eyes (e.g., choriocapillaris) by one of the ophthalmologic procedures described below. The additional tests or screening can also include detection of autoantibodies against additional macular degeneration-associated molecules that have not been examined. The additional tests can also include analyses of abnormal activity or abnormal expression level of other macular degeneration-associated molecules, such as complement pathway molecules as described in the commonly assigned, co-pending U.S. patent application Ser. No. 09/845,745. The additional tests can also include examination of the presence of macular degeneration-associated genetic markers, drusen-associated phenotypic markers, or drusen-associated genotypic markers that often correlate with macular degeneration-related disorders, as discussed below.

Macular degeneration-associated genetic markers are genetic loci which are shown to be correlated with a risk of developing a macular degeneration-related disorder. Such markers have been described, e.g., in WO 00/52479, and include, e.g., chromosome 2p16-p21 for Malattia Leventinese (e.g., a Arg345Trp mutation in the EFEMP1 gene which encodes fibulin 3; Stone et al., Nat. Genetics 22:199-2-2, 1999); 1p21-q13, for recessive Stargardt's disease or fundus flavi maculatus (Allikmets et al. Science 277:1805-1807, 1997); 1q25-q31, for recessive AMD (Klein et al., Arch. Ophthalmol. 116:1082-1088, 1988); 2p16, for dominant radial macular drusen, dominant Doyne honeycomb retinal degeneration, or Malattia Leventinese (Edwards et al., Am. J. Ophthalmol. 126:417-424, 1998); 6p21.2-cen, for dominant macular degeneration, adult vitelloform (Felbor et al. Hum. Mutat. 10:301-309, 1997); 6p21.1 for dominant cone dystrophy (Payne et al. Hum. Mol. Genet. 7:273-277, 1998); 6q, for dominant cone-rod dystrophy (Kelsell et al. Am. J. Hum. Genet. 63:274-279, 1998); 6q11-q15, for dominant macular degeneration, Stargardt's-like disease (Griesinger et al., Am. J. Hum. Genet. 63:A30, 1998); 6q14-q16.2, for dominant macular degeneration, North Carolina Type (Robb et al., Am. J. Ophthalmol. 125:502-508, 1998); 6q25-q26, dominant retinal cone dystrophy 1 ((http://www3.ncbi.nlm.nih.gov/omim, (1998)); 7p21-p15, for dominant cystoid macular degeneration (Inglehearn et al., Am. J. Hum. Genet. 55:581-582, 1994); 7q31.3-32, for dominant tritanopia, protein: blue cone opsin (Fitzgibbon et al., Hum. Genet. 93:79-80, 1994); 11p12-q13, for dominant macular degeneration, Best type (bestrophin) (Marquardt et al., Hum. Mol. Genet. 7:1517-1525, 1998); 13q34, for dominant macular degeneration, Stargardt type (Zhang et al., Arch. Ophthalmol. 112:759-764, 1994); 16p12.1, for recessive Batten disease (Munroe et al., Am. J. Hum. Genet. 61:310-316, 1997); 17p, for dominant areolar choroidal dystrophy (Lotery, A. J. et al., Ophthalmol. Vis. Sci. 37:1124, 1996); 17p13-p12, for dominant cone dystrophy, progressive (Small et al., Am. J. Ophthalmol. 121:13-18, 1996); 17q, for cone rod dystrophy (Klystra, J. A. et al., Can. J. Ophthalmol. 28:79-80, 1993); 18q21.1-q21.3, for cone-rod dystrophy, de Grouchy syndrome (Manhant, S. et al., Am. J. Hum. Genet. 57: A96, 1995; Warburg, M. et al., Am. J. Med. Genet. 39:288-293, 1991); 19q13.3, for dominant cone-rod dystrophy; recessive, dominant and 'de novo' Leber congenital amaurosis; dominant RP; protein: cone-rod otx-like photoreceptor homeobox transcription factor (Li et al., Proc. Natl. Acad. Sci USA 95:1876-1881, 1998); 22q12.1-q13.2, for dominant Sorsby's fundus dystrophy, tissue inhibitors of metalloproteases-3 (TIMP3) (Felbor et al., Am. J. Hum. Genet. 60:57-62, 1997); and Xp11.4, for X-linked cone dystrophy (Seymour et al., Am. J. Hum. Genet. 62:122-129, 1998).

Drusen-associated phenotypic or genotypic markers that correlate with macular degeneration-related disorders or drusen associated disorders have been described in WO 00/52479. Examples of drusen-associated phenotypic markers include: RPE dysfunction and/or death, immune mediated events, dendritic cell activation, migration and differentiation, extrusion of the dendritic cell process into the sub RPE space (e.g. by detecting the presence or level of a dendritic cell marker such as CD68, CD1a and S100), the presence of geographic atrophy or disciform scars, the presence of choroidal neovascularization and/or choroidal fibrosis, especially in the macula. Examples of drusen-associated genotypic markers include mutant genes and/or a distinct pattern of differential gene expression. Genes expressed by dysfunctional and/or dying RPE cells include: HLA-DR, CD68, vitronectin, apolipoprotein E, clusterin and S-100. Genes expressed by choroidal and RPE cells in AMD include heat shock protein 70, death protein, proteasome, Cu/Zn superoxide dismutase, cathepsins, and death adaptor protein RAIDD. Other markers involved in immune mediated events associated with drusen formation include leukocytes, dendritic cells, myofibroblasts, type VI collagen, and chemokines and cytokines. In addition to complement proteins, other molecules associated with drusen include: immunoglobulins, amyloid A, amyloid P component, HLA-DR, fibrinogen, Factor X, prothrombin, C reactive protein (CRP) apolipoprotein A, apolipoprotein E, antichymotrypsin, thrombospondin, and vitronectin. Markers of drusen associated dendritic cells include: CD1a, CD4, CD14, CD68, CD83, CD86, and CD45, PECAM, MMP14, ubiquitin, and FGF. Important dendritic cell-associated accessory molecules that participate in T cell recognition include ICAM-1, LFA1, LFA3, and B7, IL-1, IL-6, IL-12, TNFα, GM-CSF and heat shock proteins. Markers associated with dendritic cell expression include: colony stimulating factor, TNFα, and IL-1. Markers associated with dendritic cell proliferation include: GM-CSF, IL-4, IL-3, SCF, FLT-3 and TNFα. Markers associated with dendritic cell differentiation include IL-10, M-CSF, IL-6 and IL-4. Markers of choroid fibrosis include: a decrease in BIG H3, increase in β1-integrin, increase in collagen (e.g. collagen 6 α2 and collagen 6 α3), increase in elastin, and an increase in human metalloelastase (HME).

Additional tests or screening can also include examination with one or more ophthalmologic procedures, such as fundus fluorescein angiography (FFA), indocyanine green angiography (ICG), fundus ophthalmoscopy or photography (FP), electroretinogram (ERG), electrooculogram (EOG), visual fields, scanning laser ophthalmoscopy (SLO), visual acuity measurements, dark adaptation measurements or other standard method. Ophthalmologic procedures have been used to evaluate patients with various macular degeneration-related disorders. For example, Spraul et al. (Klin Monatsbl Augenheilkd, 21:141-8, 1998) described the use of optical coherence tomography for evaluation of patients with AMD; Kohno et al. (Bull Soc Belge Ophtalmol, 259(-

HD-):81-8, 1995) reports detection of choroidal neovascularization in age-related macular degeneration using subtraction methods in indocyanine green angiography; Kuck et al. (Retina, 13:36-9, 1993) discussed examination of patients with exudative age-related macular degeneration and clinical signs of subretinal neovascular membranes were examined by scanning laser fluorescein angiography; Kaluzny et al. (Klin Ocma, 101:355-9, 1999) and Yuzawa et al. (Eur J Ophthalmol, 2:115-21, 1992) described the use of indocyanine green (ICG) angiography in diagnosis of occult choroidal neovascularization in age-related macular degeneration; Lubinski et al. (Klin Oczna, 100:263-8, 1998) reported evaluation of foveal cone function in healthy subjects and patients with different macular diseases with foveal cone electroretinogram (FCERG, a type of focal ERG); and Kakehashi et al. (Jpn J Ophthalmol, 40:116-22, 19960 discussed differential diagnosis of macular breaks using the scanning laser ophthalmoscope (SLO). All these procedures can be used in conjunction with the diagnostic methods of the present invention. For instance, fundus autofluorescein angiography can be used for identifying defects at the level of the RPE (see, e.g., Delori et al., Invest Ophthalmol, 14:487-92, 1975; Holz et al., Graefes Arch Clin Exp Ophthalmol, 237:145-52, 1999; and Delori et al., Invest Ophthalmol Vis Sci, 36:718-29, 1995).

Further tests or screening can also include monitoring for clinical symptoms of a macular degeneration-related disorder, which include presence of drusen, retinal pigmentary changes, and includes early stages of degeneration of the macula in which vision has not been significantly affected ("dry" macular degeneration), atrophic macular degeneration, and exudative disease in which neovascularization is prevalent ("wet" macular degeneration). Further screening can also include analyses of family history for related family members with macular degeneration-related disorders, and/ or genetic analyses of polymorphisms associated with macular degeneration-related disorders (as described above). As a result of one or more of these additional tests, the initial diagnosis based on abnormal complement activities or expression levels can be confirmed, and the particular type of macular degeneration-related disorder affecting a subject can be identified.

IV. Identifying Genetic Causes of Macular Degeneration-Related Disorders

Identification of macular degeneration-related autoantigens also provide means for further understanding the genetic nature of macular degeneration-related disorders, especially those for which mutant genes have not been identified (e.g., AMD). Similar to many other diseases, mutations in the genes which encode the macular degeneration-associated autoantigens (e.g., fibulin 3, vitronectin, complement pathway associated proteins described in application Ser. No. 09/845,745, or the other RPE autoantigens described in the Examples) can be the genetic cause of macular degeneration-related disorders. For example, a Arg345Trp mutation in the EFEMP1 gene has been shown to be correlated with Malattia Leventinese. Also, it is known that a number of diseases are due to deficiencies in proteins associated with the complement pathway, and the deficiency is often due to mutations in the complement protein. Examples of such disease include: SLE like symptoms (point mutation in C1q); hereditary angioedema (mutations and polymorphisms in C1q inhibitor); SLE (deletions in C2); pyogenic infections (61 bp deletion in exon 18 of C3 gene); membranoproliferative (C3); glomerulonephritis (C3); partial lipodystrophy (C3); SLE (frameshift in C4a); predisposition to Neisseria (C6: stop codon insertion leading to truncated gene product); meningitis and Neisseria infection (Factor P (Properdin): point mutations; X-linked); autosomal recessive atypical hemolytic uremic syndrome (Factor H: point mutations); aplastic anemia and paroxysmal nocturnal hemoglobinuria (PNH) (CD59: deletion in codon 16, also single base pair mutations; and PNH (CD55, deletion point mutation).

To identify the genetic causes of macular degeneration-related disorders (e.g., AMD), the specific autoantigens or immune complexes identified, e.g., as described in Examples, can be subject to further analysis. For example, the identity and sequence information of the autoantigens can be revealed by standard amino acid sequencing procedures (e.g., Current Protocols in Molecular Biology, Ausubel, F. M. et al., 1999, John Wiley & Sons, Inc., New York) as well as other methods for protein identification (e.g., matrix assisted-laser desorption ionization mass spectrometry, as disclosed in Example 11). Polynucleotide primers can be generated and used to clone the genes which encode these autoantigens with standard techniques routinely practiced in molecular biology (Sambrook et al., Molecular Cloning A Laboratory Manual, 3rd Ed., 2000, Cold Spring Harbor Laboratory Press). The nucleotide sequences of such autoantigens can thus be obtained. The sequences can be compared with the DNA sequences from the genomic databases (e.g., GenBank). Any mutation or polymorphism identified in the autoantigen-encoding sequence relative to a wild type sequence would indicate that the corresponding gene is a likely candidate which causes the macular degeneration-related disorder (e.g., AMD). Tissues from donors with or without macular degeneration-related disorders can be used for confirmation of gene mutations and aberrant pathways.

V. Therapeutics: Inducing Tolerance

Identification of the macular degeneration-related autoantigens provides means of treating or preventing macular degeneration through induction in a subject of tolerance to the specific macular degeneration-related autoantigen (e.g., fibulin 3 with a Arg345Trp mutation). Induction of immunological tolerance is a therapeutic or preventive method in which a lack of immune responses to certain antigens is achieved. Various autoantigens can be utilized to induce tolerance in a subject according to the present invention. Exemplary autoantigens include fibulin-3, vitronectin, β crystallin A2, β crystallin A3, β crystallin A4, β crystallin S, glucose-regulated protein 78 kD (GRP-78), calreticulin, complement 1q binding protein/hyaluronan-binding protein, 14-3-3 protein epsilon, serotransferrin, albumin, keratin, pyruvate carboxylase, and villin 2.

Tolerance is imparted by elimination of, or induction of nonresponsiveness in, autoimmune T or B cells. It can be induced in part by activation of suppressor mechanisms by the soluble fragment, which suppress cellular and humoral responses directed toward the fragment. See, e.g., Kaufman et al., (1993), Nature 366:69-71; Tisch et al. (1993), Nature 366, 71-75. Suppression of humoral responses is believed to be of particular importance in preventing impairment of neurons in stiff man syndrome. In some methods, the generation of nonresponsiveness and consequent impairment of autoimmune response is facilitated by coupling a macular degeneration-related polypeptide to immunoglobulins, e.g., IgG, or to lymphoid cells from the patient being treated. See Bradley-Mullen (1982), Annals N.Y. Acad. Sci. 392: 156-166.

Tolerance against a given macular degeneration-related autoantigen can be induced by administering to a subject a tolerogenic form of the macular degeneration-associated molecule (e.g., fibulin 3 or vitronectin). The tolerance-inducing form of a macular degeneration-related antigen can be prepared with various methods described in the art. For example, U.S. Pat. No. 5,681,571 teaches a method of inducing immunological tolerance in an individual against a specific antigen by administering through a mucosal route the antigen that is linked to the B subunit of cholera toxin (or the B subunit of heat-labile enterotoxin of *Escherichia coli*). U.S. Pat. No. 5,681,571 discloses a method for inducing antigen-specific immune tolerance by depletion of resident thymic antigen presenting cells (APCs) and re-population of thymus with new APCs containing the antigen for tolerance. Tolerance can also be induced via dendritic cell immunization, as described in, e.g., Thomson et al., Stem Cells 13:622-39, 1995; and Hayamizu et al., Transplantation 66:1285-91, 1998. Additional methods for inducing tolerance have been described in U.S. Pat. Nos. 6,153,203, 6,103,235, and 5,951,984.

To induce tolerance, it is to be noted that the nature of response (i.e., immunogenic or tolerogenic) depends on the dose, physical form and route of administration of antigen. High or low doses of an antigen often lead to immune tolerance, whereas intermediate doses may be immunogenic. Monomeric forms of antigen are usually tolerogenic, whereas high molecular weight aggregates are likely to be immunogenic. Oral, nasal, gastric or intravenous injection of antigen frequently leads to tolerance, whereas intradermal or intramuscular challenge especially in the presence of adjuvants favors an immunogenic response. See Marx, Science 252, 27-28 (1991); Trentham et al., Science 261, 1727-1730 (1993); Metzler & Wraith, International Immunology 5, 1159-1165 (1993); Cobbold et al., WO90/15152 (1990).

Oral administration of an autoimmune antigen has been shown to protect against development of experimental allergic encephalomyelitis in animal models, and to suppress rheumatoid arthritis in animal models and in clinical trials. See Marx, Science 252, 27-28 (1991); Trentham et al., Science 261, 1727-1730 (1993) (each of which is incorporated by reference in its entirety for all purposes). Nasal administration of an autoantigen has also been reported to confer protection against experimental allergic encephalomyelitis, and is a preferred route for administration of small fragments. See Metzler & Wraith, International Immunology 5, 1159-1165 (1993). In some methods, immune tolerance is induced under cover of immunosuppressive treatment. See Cobbold et al., WO90/15152 (1990).

VI. Kits

The present invention also provides kits for detecting a predisposition for developing a macular degeneration-related disorder. The invention also provides kits for testing tolerance that is induced using methods as described above. Also provided are kits for testing sensitization to an antigen using an array of suspected antigens to challenge peripheral monocytes or lymphocytes. Methods employed in the latter kits include a lymphocyte proliferation assay (LPA) as described, e.g., in Example 7.

For example, kits for carrying out the diagnostic methods disclosed above can be produced in a number of ways. Kits for testing tolerance or sensitization to an antigen can be produced with no or minor modifications. Thus, some of the diagnostic kits comprise (a) at least one macular degeneration-associated molecule (e.g., fibulin 3 or vitronectin) or an antigenic fragment thereof conjugated to a solid support and (b) a detectably labeled binding molecule that can binds to the human autoantibody. In some kits, the binding molecule can comprise an antibody (e.g., goat anti-human immunoglobulin) bound to a detectable compound, including, but not limited to, an enzyme, radioactive molecule, or fluorescent compound. In some kits of the present invention, the binding molecule is bound to an enzyme that can react with an added substrate to yield a detectable (e.g., a colored) product. Such kits can preferably include a supply of the substrate. In some kits, the binding molecule is a detectably labeled protein A or protein G.

In other diagnostic kits, the antigen is not bound to a solid support. Such kits can comprise (a) a macular degeneration-associated molecule (e.g., fibulin 3 or vitronectin) or its antigenic fragment that is detectably labeled, and (b) a specific binding molecule bound to a solid support. In such kits, the binding molecule (e.g., anti-human immunoglobulin, protein A, or protein G) is immobilized to a solid phase such as sepharose or agarose in order to facilitate separation of antigen-antibody complex from the liquid sample.

The diagnostic kits are presented in a commercially packaged form as a combination of one or more containers holding the necessary reagents, as a composition or admixture where the compatibility of the reagents will allow. The kits can also include other materials as known in the art, such as buffers, diluents, and standards that are useful as washing, processing and indicator reagents. The diagnostic kit can further include agents for reducing background interference in a test and protein stabilizing agents, e.g., polysaccharides. The kits can also include a sheet of printed instructions for carrying out the test.

Preferably, the macular degeneration-associated molecules used in the kits are fibulin-3, vitronectin, $\beta$ crystallin A2, $\beta$ crystallin A3, $\beta$ crystallin A4, $\beta$ crystallin S, calreticulin, 14-3-3 protein epsilon, serotransferrin, albumin, keratin, pyruvate carboxylase, or villin 2. When more than one antigen is employed in a diagnostic kit, the corresponding binding molecules (e.g., goat anti-human immunoglobulins or protein A) are usually conjugated to different detectable labels. For kits designed for diagnosing AMD, the antigens packaged in the kits preferably contain at least vitronectin (or its antigenic fragments). For kits to be used for diagnosis of Malattia Leventinese, the preferred antigens contained in the kits are fibulin 3, $\beta$ crystallin A2, $\beta$ crystallin A3, $\beta$ crystallin A4, $\beta$ crystallin S, glucose-regulated protein 78 kD (GRP-78), calreticulin, hyaluronan-binding protein, 14-3-3 protein epsilon, serotransferrin, albumin, keratin, pyruvate carboxylase, and villin 2.

The practice of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Sambrook et al., Molecular Cloning A Laboratory Manual, 3rd Ed., 2000, Cold Spring Harbor Laboratory Press; Hogan et al. (Manipulating the Mouse Embryo: A Laboratory Manual (1986), *Cold Spring Harbor Laboratory Press*, Cold Spring Harbor, N.Y.; See U.S. Pat. No. 4,683,195; *DNA Cloning*, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., *Cold Spring Harbor Laboratory*, 1987; Methods In Enzymology, Vols. 154 and 155, Wu et al., eds., Academic Press Inc., N.Y.; Immunochemical Methods In Cell And Molecular Biology (Mayer and Walker, eds., *Academic Press*, London, 1987; Handbook Of Experimental Immunology, Volumes I-IV, D. M. Weir and C. C. Blackwell, eds., 1986.

Thus, many modifications and variations of this invention can be made without departing from its spirit and scope. The specific examples described herein are for illustration only and are not intended to limit the invention in any way.

All publications, figures, patents and patent applications cited herein are hereby expressly incorporated by reference for all purposes to the same extent as if each was so individually denoted.

EXAMPLES

Example 1

Autoantibodies in the Sera of Donors with AMD and/or Drusen

It has been observed that serum autoantibodies are present in some AMD subjects. In order to address the role of autoantibodies in drusen biogenesis and AMD, a series of experiments were performed using enriched drusen preparations in order to identify anti-drusen/Bruch's membrane/RPE autoantibodies that might be present in the sera of donors with AMD and/or drusen.

Protein extracts from an enriched drusen preparation (DR+) obtained by debridement of Bruch's membrane with a #69 Beaver blade and from a control (DR−) preparation were prepared using PBS with proteinase inhibitor cocktail and mild detergent. Proteins were separated by molecular weight using 10-20% gradient mini SDS gels (Amresco) and transferred to PVDF membranes for Western blot analysis. PVDF strips with human retinal proteins from 50 normal human retinas were also used for detection of any anti-retinal autoantibodies in the donor sera.

Sera from the same eight donors described above were screened. Serum from one AMD donor (#90-98) positively labeled a band in the RPE (both DR+ and DR−) and RPE/choroid preparations of approximately 35 kDa. A second band of approximately 60 kDa was labeled weakly only in the DR+ protein extract. Sera from an AAA donor (#189-97) reacted with a protein(s) of approximately 53 kDa. This band labeled in all three protein extracts. There was one band of approximately 64 kDa that this serum sample labeled only in the DR+ sample.

The presence of serum anti-drusen/RPE autoantibodies in donors with AMD and/or drusen further indicates a possible role for shared immune-mediated processes in these conditions.

Example 2

Analyses of Autoantibodies in the Sera of Living AMD Subjects

In order to determine whether the sera of AMD subjects possesses autoantibodies or alterations in the abundance and/or mobility of serum proteins, plasma was collected from 20 subjects with clinically-diagnosed AMD and from 20 unaffected subjects to serve as controls.

For some experiments, sera were separated by SDS-PAGE and proteins were visualized with either silver stain or Coomassie blue, or (for preparative purposes) proteins were transferred to PVDF membranes for amino acid sequencing. Abnormalities of serum proteins were detected in a subset of AMD donors. These differences included the presence of "additional" bands in the sera of some AMD subjects (molecular weights of ~25, 29, 30 and 80 kDa) that were not present in control donors. Amino acid sequencing of these molecules revealed N-terminal sequences consistent with haptoglobin (25 kDa) and immunoglobulin kappa (29 kDa), lambda (30 kDa), and gamma (80 kDa) chains.

In a second set of experiments, sera from AMD and control donors was screened for the presence of autoantibodies against RPE and choroid proteins. As an extersion of experiments in which weak-moderate immunoreactivity of drusen in tissue sections was previously observed, purified vitronectin (Suzuki et al., EMBO J, 4:2519-24 1985) was electrophoretically separated and blotted onto PDVF. Because vitronectin had previously been identified as a drusen-associated molecule (as detailed in Example 1), the sera from AMD subjects was then evaluated for the presence of anti-vitronectin immunoreactivity. Strong labeling of both the 65 kDa and 75 kDa vitronectin species was identified in these sera, indicating that AMD sera contain autoantibodies directed against at least some drusen-associated molecules and/or Bruch's membrane constituents.

As an additional approach toward the identification of AMD autoantibodies and their targets in ocular tissues, RPE-choroidal proteins from one donor with large numbers of drusen and a nine month old donor were separated electrophoretically according to molecular weight and transferred to nitrocellulose. Proteins were then immunolabeled with either sera from 3 AMD donors or polyclonal antiserum directed against vitronectin. The AMD sera reacted with bands of roughly 65, 150 and 200 kDa only in the sample from the donor with numerous drusen. These results indicate that age and/or the presence of drusen leads to an increase in AMD autoantigens.

Example 3

Autoantibodies Directed against RPE, Retina, and Fetal Eye Proteins in a Patient with Malattia Leventinese Proteins extracted from the neural retinal, isolated RPE cells, and an entire fetal human eye (96 day) were separated by two-dimensional gel electrophoresis followed by either (a) transfer of the separated proteins to PVDF membranes or (b) silver staining of the 2D gel with a modified solution that is compatible with Matrix Assisted Laser Desorption Ionization (MALDI) mass spectrometry analyses.

Blots were probed with human serum derived from a patient with the early onset macular dystrophy Malattia Leventinese, followed by detection of immobilized primary antibodies with alkaline phosphatase-conjugated antibodies directed against human immunoglobulins, and positively labeled spots were matched with the corresponding spots on the silver-stained gels. Silver-stained protein spots corresponding with autoantigens on the Western blots were excised and digested in a solution containing endoproteinase Lys-c/Trypsin, and the resultant peptides were analyzed by matrix assisted-laser desorption ionization mass spectrometry, a technique that permits the identification of a protein based upon the molecular weights of its peptides (Wheeler et al., Electrophoresis, 17(3):580-7 1996). MALDI-MS can be used as a complement to internal amino acid sequencing. In J. Walker (Ed.), The Protein Protocols Handbook (pp.

541-555, Totowa: Humana Press). This technique resulted in the identification of a number of autoantigens within these tissues:

Seven proteins that have been identified from the fetal eye tissue are:

(i) #1 and #2—MW=27 KD and 25 KD—beta crystallin A4 (Slingsby et al., Exp Eye Res, 51:21-6, 1990);

(ii) #3—MW=25 KD—beta crystallin A2 and trace of beta crystallin A4 (Slingsby et al., supra);

(iii) #4—MW=26 KD—beta crystallin A3 (Slingsby et al., supra);

(iv) #5—MW=18 KD—beta crystallin S (Quax-Jeuken et al., EMBO J, 4(10):2597-602, 1985);

(v) #6—MW=26 KD—beta crystallin A4; and (vi) #7—MW=80 KD—78 KD glucose-regulated protein Kiang et al., Chin J Physiol, 40:213-9, 1997)

Six proteins were identified from the retinal protein extract:

(i) #1. MW=60 KD-calreticulin (Kovacs et al., Biochemistry, 37(51):17865-74, 1998

(ii) #2. MW=33 KD—complement component 1 (a.k.a glycoprotein GC1QBP, hyaluronan-binding protein; Lynch et al., FEBS Lett, 418(1-2):111-4, 1997)

(iii) #3. MW=29 KD—14-3-3 protein epsilon (Yamanaka et al., Proc Natl Acad Sci USA, 94:6462-7, 1997)

(iv) #4. MW=85 KD—serotransferrin (Campbell et al., J Biol Chem, 252:5996-6001, 1977)

(v) #5. MW=80 KD—albumin (vi) #6. MW=75 KD—keratin (Hintner et al., J Invest Dermatol, 93:656-61, 1989)

Two proteins were identified from the RPE protein extract:

(i) #1. MW=120 KD—pyruvate carboxylase; and (ii) #2. MW=88 KD—hypothetical protein DKFZp762H157.1 (also called villin 2; Burgess et al., J. Immunol., 1992, 149: 1847-1852, and U.S. Pat. No. 5,773, 573).

Example 3

Autoantibodies Directed against RPE, Choroidal, and Retinal Proteins in a Patient with AMD In a separate set of experiments, the serum from donor #189-97 (diagnosed with AMD) was employed to probe protein extracts from human choroid (donor 325-00, 77 CF), RPE (donor 318-00, 67 CM) and retina (donor 294-00, 84 CF, AMD) on blots following two-dimensional gel electrophoresis, as described above. Several positively-labeled spots, corresponding to putative autoantigens, were identified. The characteristics of these protein spots were as follows:

Choroidal extract proteins:

(i) three spots were identified with an approximate MW of 86 KD, PI between 5 and 6;

(ii) four spots were identified with an approximate MW of 60 KD, PI between 7 and 8; some co-migrate with fibulin 3 antibody reactive spots.

(iii) five spots were identified with an approximate MW of 45 KD, PI between 6 and 7;

(iv) 6 spots were identified with an approximate MW between 30 and 43 KD, PI between 4.5 and 6;

(v) 2 spots were identified with an approximate MW of 33 and 35 kD, PI an approximate 7.5;

(vi) 1 spot was identified with MW of 29 KD, PI between 5 and 5.5; and (vii) 1 spot was identified with an approximate MW of 25 KD, PI approximately 7.5.

RPE extract proteins:

(i) three spots were identified with an approximate MW of 86 KD, PI between 5 and 6;

(ii) three confluent spots were identified with an approximate MW of 95-100K, PI 6.5-7;

(iii) two spots were identified with an approximate MW of 94 KD, PI between 5 and 6;

(iv) one spot was identified with an approximate MW of 60 KD, PI~4.5; co-migrates with fibulin 3 antibody reactive spots.

(v) 2 spots were identified with an approximate MW of 33 and 35 kD, PI~7.5; and (vi) 5 spots were identified with an approximate MW between 35 and 43 KD, PI between 6 and 7;

Retinal extract proteins:

(i) thee confluent spots were identified with an approximate MW of 95-100K, PI 6.5-7;

(ii) 2 spots were identified with an approximate MW of 33 and 35 kD, PI~7.5;

(iii) one spot was identified with an approximate MW of 30-33 KD, PI~7;

(iv) several confluent spots were identified with an approximate MW of 60 KD, PI 4-5;

(v) one spot was identified with an approximate MW of 28-30 KD, PI 4.5-5; and (vi) several spots were identified between 28 and 65 KD with PI from 4 and 7.5.

Example 4

Additional Serological Tests for Markers in Drusen Biogenesis and AMD

Visual acuity measurements, stereo macula photos, and peripheral photos can be taken at the beginning of the study and every six months thereafter. Blood and sera can be drawn when subjects enter the study and every 6-12 months thereafter. DNA can be prepared from a portion of each blood sample for future genetic studies. The presence of serum autoantibodies and immune complexes can be determined using standard protocols. In addition, sera can be reacted with tissue sections derived from donors with and without AMD, followed by a secondary antibody that has been adsorbed against human immunoglobulins. Western blots of retina/RPE/choroid from AMD and non-AMD donors can also be incubated with serum samples to identify specific bands against which autoantibodies react.

The presence of antibodies directed against the following proteins (many observed in other age-related conditions and/or MPGN) can also be determined: type IV collagen, glomerular basement membrane, neutrophils, cytoplasm (c-ANCA, p-ANCA), C3 convertase (C3 nephritic factor), alpha-1 anti-trypsin levels (decreased in MPGN), epsilon 4 allele, apolipoprotein E, GFAP, ANA, serum senescent cell antigen, S-100, type 2 plasminogen activator, alpha-1-antichymotrypsin, SP-40,40, endothelial cell, parietal cell, mitochondria, Jo-1, islet cell, inner ear antigen, epidermolysis Bullosa Acquista, endomysial IgA, cancer antigen 15-3, phospholipid, neuronal nucleus, cardiolipin, and ganglioside.

In addition to autoantibodies against complement components, sera from the subject can be reacted with tissue sections derived from donors with and without AMD, followed by a secondary antibody that has been adsorbed against human immunoglobulins. Western blots of retina/

RPE/choroid from AMD and non-AMD donors can also be incubated with serum samples to identify specific bands against which autoantibodies react.

Further, other than autoantibodies, levels of the following proteins, additional indicators of autoantibody responses, chronic inflammation and/or acute phase responses, can be assayed by a clinical diagnostic laboratory. These can include Bence Jones protein, serum amyloid A, M components, CRP, mannose binding protein, serum amyloid A, C3a, C5a, other complement proteins, coagulation proteins, fibrinogen, vitronectin, CD25, interleukin 1, interleukin 6, and apolipoprotein E. Serum protein electrophoresis, lymphocyte transformation, sedimentation rate, and spontaneous, whole blood, white cell count can also be measured. Other proteins that provide additional indication of autoantibody responses, chronic inflammation and/or acute phase responses, can also be assayed.

Example 5

Fibulin Protein and mRNA Expression and Distribution in the Human Eye

The fibulin family of glycoproteins includes 5 members described to date, all of which appear to be secreted matrix components with a variable number of EGF repeat domains. Their interactions with diverse matrix components, including basal lamina components and tropoelastin, suggest a role in matrix assembly.

In order to assess the synthesis and distribution of fibulins in the human eyes, various molecular biological, biochemical, immunological, and immunohistochemical studies on human donor eyes were conducted. As demonstrated below, these data collectively indicate that fibulin mRNAs and proteins are synthesized by neural retina, RPE, and choroid cells, and that fibulin-3 accumulates in basal deposits adjacent to Bruch's membrane with age. These data indicate a mechanism for the role of mutated fibulin-3 in the pathogenesis of ML, particularly in the biogenesis of drusen and/or other sub-RPE, pathologic lesions. The data also indicate that fibulin-3 is found in the same location as C5b-9 complexes and other modulators of the complement cascade, suggesting that mutant fibulin 3 may participate in activation and subsequent damage.

1. Protein Localization—CLSM

In order to assess the distribution of fibulin-3 protein in human donor eyes, polyclonal antibodies directed against fibulin-3 and fibulin-4 (obtained from Dr. Gunter Kostka, Max Planck Institute, Martinsried, Germany) were employed to immunolabel tissue sections for examination by confocal laser scanning microscopy.

Drusen was not strongly labeled with fibulin-3 antibodies. Weak, diffuse labeling of the choroid and a stronger labeling of the ECM surrounding large choroidal vessels was noted with this antibody. In addition, intense labeling of a domain at the basal surface of the RPE was detected. To examine the specific location of fibulin-3 in Bruch's membrane and sub-RPE deposits, sections were simultaneously labeled with antibodies directed against fibulin-3 and either laminin—to detect basal laminae—or β2 integrin (to demarcate the basal surface of the RPE plasma membrane). Labeling within Bruch's membrane in some cases colocalized with laminin, suggesting an association with the basal lamina. An additional pattern was also noted, in which fibulin-3 labeling was confined to domains between the RPE basal lamina and the RPE plasma membrane (corresponding to the location of basal laminar deposits, or BLD).

An antibody directed against fibulin-4 was also examined for its immunoreactivity with the retina-RPE-choroid complex. These studies revealed a similar, but weaker, labeling of BLD/Bruch's membrane than observed with fibulin-3. In addition, fibulin-4 antibody reaction with the choroid was less diffuse than observed for fibulin-3.

2. Protein Localization—IH/BLD

Because of the apparent localization of fibulin-3 within the sub-RPE space corresponding to BLD, subsequent studies were performed on sections of eyes from donors on whom transmission electron microscopy had previously shown to possess very significant accumulations of BLD (measurable at the light level of resolution). Tendril-like formations within BLD in these donors were found to possess immunoreactivity for fibulin-3, confirming previous dual-labeling experiments. This labeling was most heavily concentrated on the apical (RPE-side) aspect of the deposits, whereas lipid accumulations—assessed by Sudan black B staining of adjacent tissues—was found to be limited to the basal (choroidal) aspect of the BLD.

3. Protein Expression—Western Blot Analyses

Western blot analysis was used to detect fibulin-3 in protein extracts from human retina, RPE and RPE/choroid. These tissues were homogenized in mild detergent (2% octylglucoside), sonicated, and the clear supernatants obtained after high speed centrifugation were used for electrophoresis. Proteins separated by molecular weight using SDS-PAGE were transferred to PVDF membranes and probed with rabbit anti-fibulin-3 antibodies, diluted 1:1000. Anti-rabbit alkaline phosphatase-conjugated secondary antibodies were used at a dilution of 1:2000. Anti-fibulin-3 antibodies labeled a single band of approximately 55 kDa in all three tissues. These bands correspond with the predicted published molecular weight of fibulin-3.

4. mRNA Expression—RT-PCR and Isoforms

In order to determine whether fibulin mRNAs are expressed in ocular cell types associated lying adjacent to Bruch's membrane, total RNA was isolated from human neural retina, RPE, and RPE-choroid (RPE/Ch) tissues. The RNA was subsequently reverse-transcribed and the resultant cDNA was amplified using fibulin primer pairs. RT-PCR analyses have been performed to determine the presence of fibulins 1-6 in these tissues. The results obtained were as follows:

TABLE 1

Presence of fibulins 1-5 in human eye tissues

| | Retina (348-99 OS # 6) | RPE/Ch (348-99 OS # 6) | RPE (411-99 OD) | Genomic (R.M. DNA) |
|---|---|---|---|---|
| Fibulin 1 | + | + | + | − |
| Fibulin 2 | + | + | Faint +? | − |
| Fibulin 3 | + | + | + | − |
| Fibulin 4 | + | + | + | − |
| Fibulin 5 | + | + | + | − |
| Fibulin 6 | + | + | − | − |

In addition, RT-PCR analyses have been performed on fetal human tissues (donor 168-99). The results are shown in Table 2. The results indicate that transcripts encoding fibulin-3 were detected in various tissues, with the most abundant signal present in the choroid.

5. Identification of Isoforms of Fibulin-3

RT-PCR analyses have been performed on adult human liver tissue, retina, RPE, and RPE/choroid to identify any tissue-specific isoforms of fibulin-3. Table 3 summarizes the results with human liver.

TABLE 2

Presence of fibulins 1-5 in human fetal tissues

| | liver | skin | brain | lung | spleen | aorta | eye |
|---|---|---|---|---|---|---|---|
| Fibulin 1 (1F/1R) | + | + | + | + | + | + | + |
| Fibulin 2 (1F/1R) | + | + | + | −? | + | Faint + | − |
| Fibulin 3 (1F/1R) | − | − | + | − | + | − | − |
| Fibulin 3 (2F/2R) | +/− | +/− | + | − | + | + | +/− |
| Fibulin 3 (3F/3R) | +/− | + | + | − | − | + | − |
| Fibulin 3 (4F/4R) | + | + | + | + | + | + | + |
| Fibulin 3 (5F/5R1) | − | − | − | − | − | + | + |
| Fibulin 3 (5F/5R2) | +/− | + | − | − | − | + | + |
| Fibulin 4 | +/− | − | +/− | + | + | +/− | +/− |
| Fibulin 5 | + | + | + | + | + | + | + |

TABLE 3

Tissue-specific isoforms of fibulin-3 in human liver

| | | |
|---|---|---|
| Exons 1-2 | 15F/15R1 | + |
| Exons 1/2-3 | 10F/15R1 | + |
| Exons 1/2-3 | 10F/15R2 | + (2 bands) |
| Exons 1/2-3 | 15F/15R2 | + (2 bands) |
| Exons 2-3 | 13F/13R1 | − |
| Exons 2-4 | 13F/13R2 | − |
| Exons 3-4 | 14F/14R | + |
| Exons 3-5 | 14F/6R1 | + |
| Exons 4-5 | 6F/6R1 | − |
| Exons 4-6 | 6F/6R2 | + |
| Exons 5-6 | 7F/7R1 | + |
| Exons 5-7 | 7F/7R2 | + |
| Exons 6-7 | 8F/8R1 | + |
| Exons 6-8 | 8F/8R2 | + |
| Exons 7-8 | 9F/9R1 | + |
| Exons 7-9 | 9F/4R2 | − |
| Exons 8-9 | 4F/4R2 | − |
| Exons 8-10 | 1F/1R | ? |
| Exons 8-10 | 4F/4R | + |
| Exons 9-10 | 5F/5R1 | + |
| Exons 9-11 | 5F/5R2 | + |
| Exons 10-11 | 11F/11R1 | + |
| Exons 10-11+ | 2F/2R | + |
| Exons 10-12 | 11F/11R2 | + |
| Exons 11-12 | 3F/3R | + |
| Exons 11-out | 3F/12R | − |
| Exons 12-out | 12F/12R | + |

RT PCR has been performed on the following human donor ocular tissues using all of the above exon-skipping primer pairs:

Set #1: 255-99 retina and RPE/Ch
   245-99 retina and RPE/Ch
   244-99 retina and RPE/Ch
   Genomic DNA Set #2: 348-99 OS Macular and foveal retina (MFR) and RPE/Ch
   348-99 OS #7 retina and RPE/Ch
   348-99 OD RPE
   168-99 fetal human eye
   168-99 fetal human liver
   Adult human liver
   Genomic DNA These data suggest that alternatively spliced forms of fibulin-3 exist. These isoforms may harbor additional mutations associated with macular degenerations.

Example 6

Detection of Serum Autoantibodies against Fibulin in Malattia Leventinese Patients This study was aimed to determine whether the immune system recognizes defective fibulin-3 in patients with Malattia Leventinese and produces autoantibodies. A serum sample from a patient diagnosed with ML was assayed for the presence of circulating autoantibodies directed against human retinal, RPE and choroidal proteins. Western blots of proteins separated by one- and two-dimensional gel electrophoresis were employed to detect tissue antigens reactive with the serum antibodies. On one-dimensional blots, one band with an approximate molecular weight of 55-60 kDa reacted with serum antibodies on blots with retinal and choroid/RPE protein extracts. Similar results were observed on the blots with protein extracts from various adult and fetal human non-ocular tissues. These data indicate that a serum autoantibody directed against a single ocular protein is present in this patient. Moreover, the tissue distribution of the potential antigen(s) is not restricted to the eye. The size of the labeled band is that expected for fibulin-3; antibodies directed against fibulin-3 label bands of an identical size in most of the tissue extracts. On two-dimensional blots comprised of human retinal proteins, five spots/isoforms with approximate molecular weights of 55-60 kDa and isoelectric points ranging between 4 and 6.5 reacted with serum from the same patient with ML. These same spots react with a polyclonal antibody directed against fibulin-3.

Example 7

Analysis with Lymphocyte Proliferation Assay (LPA)

In order to determine whether the immune system of AMD patients is sensitized against antigens derived from the RPE, Bruch's membrane, choroidal neurosensory retina proteins, and/or fibulin 3, a series of lymphocyte proliferation assays (LPA) were performed using blood obtained from patients with and without clinical signs of AMD (included early AMD, geographic atrophy and choroidal neovascularization). LPA was performed as described in the art (e.g., Gehrz et al., Clin Exp Immunol. 37:551-7, 1979). A total of 62 samples derived from 62 clinic patients have been examined.

Briefly, mononuclear cells from patients' peripheral blood were isolated by centrifugation on a Histopaque gradient, and were subsequently collected, washed and counted. Cell concentration was adjusted to $10^6$ cells per ml and PBMCs were plated on microtiter plates at a concentration of 100 µl per well. Cells were then challenged with the following antigens: protein extracts derived from RPE, RPE-choroid, and retina (derived from donors with drusen); recombinant fibulin-3; ETNA elastin; and albumin. The lectin Phaseolus vulgaris agglutinin (PHA) was employed as a positive control mitogen for inducing proliferative responses in functionally active lymphocytes. The data are presented in Table 4. Significantly, lymphocytes collected from patients with early age-related macular degeneration (ARM) respond to fibulin 3 antigen, those with later stage geographic atrophy (GA) respond to RPE antigens, and those with later stages (AMD and choroidal neovascularization (CNV)) respond to elastin peptides. These data suggest that there may be significant differences in immune responses between individuals with geographic atrophy and those with the early and exudative form of AMD.

TABLE 4

Positive LPA in control and affected individuals (%)

|  | Control | ARM | GA | CNV | AMD |
|---|---|---|---|---|---|
| PHA | 95% | 75% | 50% | 66% | 66% |
| RPE | 10% | 16% | 75% | 11% | 22% |
| choroid | 10% | 0% | 0% | 17% | 11% |
| elastin | 40% | 42% | 0% | 45% | 55% |
| retina | 30% | 41% | 50% | 27% | 11% |
| fibulin-3 | 20% | 83% |  | 38% | 11% |
| albumin | 25% | 25% | 50% | 11% | 0% |

In a pilot study to determine the feasibility of using post-mortem human tissue for LPA analyses, whole blood and choroidal extracts were employed for LPA. A small volume (~10 cc) of whole blood was isolated from a human donor (338-01) within five hours of death. Blood was fractionated as described above and $10^6$ PBMCs/mL were plated onto microtiter plates. Cells were stimulated with PHA, to determine their innate ability to undergo mitogen induced proliferation. A stimulation index of 6.89 (0.25 µg of PHA) and 23.06 (1.0 µg of PHA) correspond to counts per minute (cpm) in PHA-stimulated cells to cpm in control untreated cells. These results indicate that LPA analyses can be used in conjunction with other multidisciplinary studies from the same human eye donor, an approach that is virtually impossible to perform in human patients.

Choroidal cells from the same donors were similarly challenged with PHA. Following the isolation of the RPE, collagenase-treated choroidal explants were incubated allowed to adhere overnight to Petri dishes in RPMI medium with 10% fetal bovine serum. Following 18-24 hours in culture, non-adherent cells, corresponding to lymphocytes and some monocytes, were removed from the cultures and incubated in microtiter plates in the presence of PHA; a positive mitogenic response was identified, in comparison to untreated controls.

What is claimed is:

1. A method for diagnosing, or identifying a predisposition to the development of, a macular degeneration-related disorder in a subject, comprising detecting in a biological sample from the subject the presence or abnormal levels of an autoantibody against, or an immune complex containing, at least one macular degeneration-associated molecule selected from the group consisting of glucose-regulated protein 78 kD (GRP-78), complement 1q binding protein/hyaluronic acid binding protein, albumin, pyruvate carboxylase, and villin 2, wherein the presence or abnormal levels of said autoantibody is indicative of a macular degeneration-related disorder or a predisposition to the development of a macular degeneration-associated molecule.

2. The method of claim 1, wherein the detecting comprises
   contacting the biological sample with said at least one macular degeneration-associated molecule or an antigenic fragment thereof, and
   detecting a specific interaction between the autoantibody and the at least one macular degeneration-associated molecule or an antigenic fragment thereof.

3. The method of claim 2, that comprises
   contacting the biological sample with said at least one macular degeneration-associated molecule or an antigenic fragment thereof, whereby a complex is formed between an autoantibody from the sample and the macular degeneration-associated molecule or antigenic fragment thereof;
   precipitating the complex and,
   detecting the complex.

4. The method of claim 2, further comprising the step of contacting the biological sample with a labeled antibody that competes with the autoantibody to form complexes with the at least one macular degeneration-associated molecule or an antigenic fragment thereof.

5. The method of claim 4, wherein the at least one macular degeneration-associated molecule or an antigenic fragment thereof is bound to a solid phase and the method further comprises the step of removing the solid phase from the biological sample to separate the complexes from unbound, labeled antibody.

6. The method of claim 1, wherein the detecting comprises precipitating the immune complex from the biological sample.

7. The method of claim 1, further comprising
   detecting a level of the autoantibody or immune complex in a control subject and
   comparing levels of the autoantibody or immune complex in the subject and the control subject.

8. The method of claim 1, wherein said biological sample is a urine, eye fluid, blood plasma, serum, whole blood, or lymph fluid from the subject.

9. The method of claim 8 wherein the biological sample is serum.

10. The method of claim 1, wherein the macular degeneration-related disorder is Malattia Leventinese.

11. The method of claim 1, wherein the macular degeneration-related disorder is age-related macular degeneration.

12. The method of claim 11 wherein the biological sample is serum.

13. The method of claim 1, further comprising examining the subject with an ophthalmologic procedure.

14. The method of claim 1 wherein the biological sample is serum and the one macular degeneration-associated molecule is glucose-regulated protein 78 kD (GRP-78).

15. The method of claim 1 wherein the biological sample is serum and the one macular degeneration-associated molecule is complement 1q binding protein/hyaluronic acid binding protein.

16. The method of claim 1 wherein the biological sample is serum and the one macular degeneration-associated molecule is albumin.

17. The method of claim 1 wherein the biological sample is serum and the one macular degeneration-associated molecule is pyruvate carboxylase.

18. The method of claim 1 wherein the biological sample is serum and the one macular degeneration-associated molecule is villin 2.

* * * * *